US008860714B2

(12) United States Patent  (10) Patent No.: US 8,860,714 B2
Sakuragi  (45) Date of Patent: Oct. 14, 2014

(54) APPARATUS AND METHOD FOR GENERATING STEREOSCOPIC VIEWING IMAGE BASED ON THREE-DIMENSIONAL MEDICAL IMAGE, AND A COMPUTER READABLE RECORDING MEDIUM ON WHICH IS RECORDED A PROGRAM FOR THE SAME

(75) Inventor: Futoshi Sakuragi, Tokyo (JP)

(73) Assignee: Fujifilm Corporation, Tokyo (JP)

( * ) Notice: Subject to any disclaimer, the term of this patent is extended or adjusted under 35 U.S.C. 154(b) by 679 days.

(21) Appl. No.: 13/017,513

(22) Filed: Jan. 31, 2011

(65) Prior Publication Data

US 2011/0235066 A1  Sep. 29, 2011

(30) Foreign Application Priority Data

Mar. 29, 2010 (JP) ................................. 2010-075196

(51) Int. Cl.
*G06T 15/00* (2011.01)
*H04N 13/00* (2006.01)
*G06T 7/00* (2006.01)
*H04N 13/04* (2006.01)

(52) U.S. Cl.
CPC .............. *H04N 13/004* (2013.01); *G06T 15/00* (2013.01); *G06T 7/0022* (2013.01); *H04N 13/0029* (2013.01); *H04N 13/0454* (2013.01); *H04N 13/0456* (2013.01)
USPC ........................................... 345/419; 359/462

(58) Field of Classification Search
USPC ............. 345/419; 359/462; 348/42, E13.059, 348/E13.04, E13.033
See application file for complete search history.

(56) References Cited

U.S. PATENT DOCUMENTS

| 5,416,510 | A | * | 5/1995 | Lipton et al. | 348/43 |
|---|---|---|---|---|---|
| 5,493,595 | A | * | 2/1996 | Schoolman | 378/41 |
| 6,219,182 | B1 | * | 4/2001 | McKinley | 359/407 |
| 7,572,009 | B2 |  | 8/2009 | Suzuki |  |
| 7,747,151 | B2 | * | 6/2010 | Kochi et al. | 396/55 |
| 8,248,462 | B2 | * | 8/2012 | Peterka et al. | 348/54 |
| 8,463,022 | B2 | * | 6/2013 | Lipton et al. | 382/154 |
| 2001/0045979 | A1 | * | 11/2001 | Matsumoto et al. | 348/43 |
| 2006/0023197 | A1 | * | 2/2006 | Joel | 355/77 |
| 2006/0164411 | A1 | * | 7/2006 | Lee | 345/419 |
| 2006/0177133 | A1 |  | 8/2006 | Kee |  |
| 2008/0055305 | A1 | * | 3/2008 | Blank et al. | 345/419 |
| 2011/0096832 | A1 | * | 4/2011 | Zhang et al. | 375/240.08 |

FOREIGN PATENT DOCUMENTS

| EP | 0860807 | 8/1998 |
|---|---|---|
| EP | 1909510 | 4/2008 |
| EP | 2239726 | 10/2010 |

(Continued)

OTHER PUBLICATIONS

DiVerdi et al. "An Immaterial Pseudo-3D display with 3D Interaction", Springer 2007.*

(Continued)

*Primary Examiner* — Kimbinh T Nguyen
(74) *Attorney, Agent, or Firm* — Young & Thompson

(57) ABSTRACT

A stereoscopic viewing image generation unit generates, using a three-dimensional medical image representing a subject as input, a stereoscopic viewing image for stereoscopic output of the subject based on a given image generation condition, and a non-stereoscopic viewing image generation unit generates a non-stereoscopic viewing image for non-stereoscopic output equivalent to the stereoscopic output based on the three-dimensional medical image and the image generation condition of the stereoscopic viewing image.

15 Claims, 19 Drawing Sheets

(56) References Cited

FOREIGN PATENT DOCUMENTS

| | | |
|---|---|---|
| JP | 62-16741 | 1/1987 |
| JP | 03-231643 | 10/1991 |
| JP | 7-210704 | 8/1995 |
| JP | 2000-107173 | 4/2000 |
| JP | 2006-121553 | 5/2006 |
| WO | 2006/056616 | 6/2006 |

OTHER PUBLICATIONS

Communication dated Aug. 30, 2012 issued by the European Patent Office in corresponding European Patent Application No. 11 152 246.2, 4 pages.

Extended European Search Report issued Apr. 7, 2011, Application No. 11152246.2.

S. Uehara et al., "High Quality 2D/3D Display", NEC Technical Journal, NEC Corporation, Japan, Apr. 2009, vol. 62, No. 2, pp. 48-52, Internet (Date of Retrieval: Jan. 14, 2010), URL:http://www.nec.co.jp/techrep/ja/journal/g09/n02/090210.pdf).

Takaki Lab, Tokyo University of Agriculture and Technology, Facility of Technology, Department of Electrical Engineering, "rResearcy & Development of Stereoscopic Display", URL:http://www.tuat.ac.jp/ e-takaki/display/display.html.

JP Office Action dated Aug. 13, 2013, with English translation; Application No. 2010-075196.

\* cited by examiner

FIG.6

| OUTPUT DESTINATION | STEREOSCOPIC VIEWING IMAGE | NON-STEREOSCOPIC VIEWING IMAGE |
|---|---|---|
| STEREOSCOPIC VIEWING SUPPORT DISPLAY UNIT | Y | N |
| STEREOSCOPIC VIEWING NON-SUPPORT DISPLAY UNIT | N | Y |
| IMAGE STORAGE SERVER | Y | Y |
| RADIOLOGY REPORT SERVER | N | Y |
| PRINTER | N | Y |

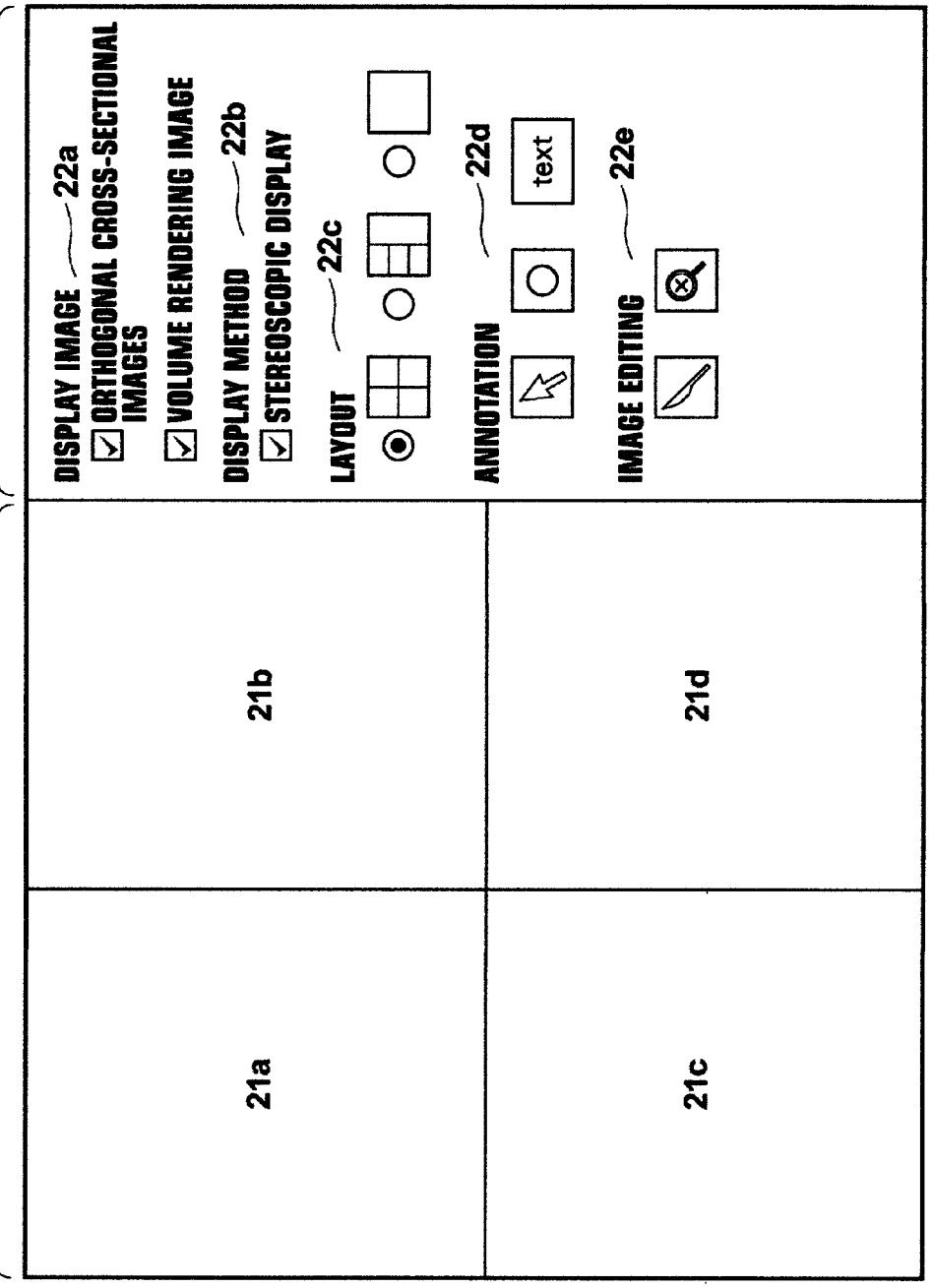

- TERMINATION OF STEREOSCOPIC VIEWING
- INSERTION OF ANNOTATION...
- IMAGE EDITING...
- PARAMETER CHANGE...

APPARATUS AND METHOD FOR GENERATING STEREOSCOPIC VIEWING IMAGE BASED ON THREE-DIMENSIONAL MEDICAL IMAGE, AND A COMPUTER READABLE RECORDING MEDIUM ON WHICH IS RECORDED A PROGRAM FOR THE SAME

BACKGROUND OF THE INVENTION

1. Field of the Invention

The present invention relates to an apparatus and method for generating a stereoscopic viewing image from a three-dimensional medical image, and a computer readable recording medium on which is recorded a program for the same.

2. Description of the Related Art

Technologies for performing a stereoscopic display are known.

For example, a stereoscopic display apparatus for a tomographic image in which two parallax images of a cross-section of a test object viewed from left and right eyes are generated based on a plurality of tomographic images obtained by CT or the like and generated parallax images are displayed on two displays is proposed as described, for example, in Japanese Unexamined Patent Publication No. 62 (1987)-016741. Here, the parallax images can be obtained, based on each of left and right viewpoints, by adding up a grey value of each pixel of tomographic images on a visual line connecting between the viewpoint and a projection plane and performing shadowing or coloring as required. When parallax images displayed by the apparatus are observed by an observer with both eyes simultaneously through a stereo viewer, the test object can be observed stereoscopically.

Further, a stereoscopic display method for a virtual endoscopic image is proposed as described, for example, in Japanese Unexamined Patent Publication No. 7 (1995)-210704. More specifically, a parallax image is generated by central projection from each of viewpoints of left and right eyes using a volume rendering method or the like and generated parallax images are displayed on a head mounted display configured such that parallax images for left eye can be viewed only by the left eye and parallax images for right eye can be viewed only by the right eye, whereby the observer can stereoscopically observe a virtual endoscopic image.

Still further, a method in which left and right parallax images representing the ocular fundus of an eye to be examined are obtained and, when a portion of an image stereoscopically displayed using these parallax images is desired to be displayed in an enlarged manner, one of the parallax image is displayed, setting of a desired zoom area in the displayed parallax image is accepted, then an area corresponding to the determined enlarging area is automatically set to the other parallax image, the determined area of each parallax image is cut out, and the area is stereoscopically displayed in an enlarged manner is proposed as described, for example, in U.S. Pat. No. 7,572,009.

The actual visual line for viewing a stereoscopically displayed image differs, in direction, from the visual line of each parallax image. Therefore, if an area is specified for one of the parallax images, as the method described in U.S. Pat. No. 7,572,009, unpleasant sensation may be felt when specifying the area or the determined area may differ from the desired area of the stereoscopically displayed image due to the difference in direction between the actual visual line for viewing the stereoscopically displayed image and the visual line of the parallax image for which the area is specified. Further, in the method described in U.S. Pat. No. 7,572,009, images serving as the basis of stereoscopic display are only two images obtained by imaging, and another image can not be used for the area specification.

Further, in order to perform a stereoscopic display, a display apparatus that supports the stereoscopic display is required. But, in actual clinical practices, not all of the apparatuses for outputting medical images support nor are required to support stereoscopic display.

The present invention has been developed in view of the circumstances described above, and it is an object of the present invention to provide an apparatus and method for generating a stereoscopic viewing image from a three-dimensional medical image capable of responding flexibly and appropriately to the case where stereoscopic output is inappropriate or not required. It is a further object of the present invention to provide a computer readable recording medium on which is recorded a program for causing a computer to perform the method.

SUMMARY OF THE INVENTION

A stereoscopic viewing image generation apparatus of the present invention is an apparatus, including:

a stereoscopic viewing image generation means for generating, using a three-dimensional medical image representing a subject as input, a stereoscopic viewing image for stereoscopic output of the subject based on a given image generation condition; and a non-stereoscopic viewing image generation means for generating a non-stereoscopic viewing image for non-stereoscopic output equivalent to the stereoscopic output based on the three-dimensional medical image and the image generation condition of the stereoscopic viewing image.

A stereoscopic viewing image generation method of the present invention is a method, including the steps of:

generating, using a three-dimensional medical image representing a subject as input, a stereoscopic viewing image for stereoscopic output of the subject based on a given image generation condition; and generating a non-stereoscopic viewing image for non-stereoscopic output equivalent to the stereoscopic output based on the three-dimensional medical image and the image generation condition of the stereoscopic viewing image.

A computer readable recording medium on which is recorded a stereoscopic viewing image generation program of the present invention is a medium having a program recorded thereon for causing a computer to perform the method described above.

In the present invention, a specific example of "stereoscopic viewing image" may be a plurality of parallax images representing a subject viewed from different viewpoints. Each parallax image may be a projection image obtained by projecting at least one pixel value of a plurality of points on a visual line extending from the viewpoint of the parallax image toward the subject. Further, the projection image may be a pseudo three-dimensional image, representing depth direction information of the subject, obtained by, for example, a volume rendering method. Still further, the stereoscopic viewing image may be an image that includes a stereoscopic viewing area for stereoscopic display and a non-stereoscopic viewing area for non-stereoscopic display.

The term "a given (stereoscopic viewing) image generation condition" as used herein refers to a condition for determining what type of stereoscopic viewing image is to be generated, which may include, for example, the number of parallax images, viewpoint positions, visual line directions, projection method (parallel projection or central projection), image generation method (volume rendering, MIP, MinIP, MPR, and the like).

The term "non-stereoscopic viewing image" as used herein refers to an image for non-stereoscopic output equivalent to the stereoscopic output. A specific example may be an image representing the subject viewed from a single viewpoint (equivalent viewpoint) equivalent to a plurality of viewpoints of a plurality of parallax images constituting a stereoscopic viewing image. Here, the equivalent viewpoint may be a point equidistant from each viewpoint, such as the midpoint of a line segment connecting between each of a plurality of viewpoints of a plurality of parallax images or a point where the distance between each viewpoint is divided at a predetermined ratio. Further, as in the stereoscopic viewing image, the non-stereoscopic viewing image may be a projection image obtained by projecting at least one pixel value of a plurality of points on a visual line extending from the equivalent viewpoint toward the subject, and the projection image may be a pseudo three-dimensional image, representing depth direction information of the subject, obtained by, for example, a volume rendering method.

When generating the stereoscopic viewing image or the non-stereoscopic viewing image as a projection image, the projection method may be a parallel projection method or a central projection method. In the case of the parallel projection method, the viewpoint of the stereoscopic viewing image or the equivalent viewpoint of the non-stereoscopic viewing image may be deemed as disposed at infinite distance in each visual line direction.

The stereoscopic viewing image generation apparatus of the present invention may further include a selective output means for selectively outputting the stereoscopic viewing image and the non-stereoscopic viewing image based on a predetermined output image selection condition. Here, the selective output means may be a means that causes either one of the stereoscopic viewing image generation means and the non-stereoscopic viewing image generation means to generate an image based on an output image selection condition and outputs the generated image or a means that causes each of the stereoscopic viewing image generation means and the non-stereoscopic viewing image generation means to generate an image regardless of the output image selection condition and selects an image to be outputted from the generated images according to the output image selection condition.

Likewise, the stereoscopic viewing image generation method of the present invention may further include the step of selectively outputting the stereoscopic viewing image and the non-stereoscopic viewing image based on a predetermined output image selection condition. Otherwise, the stereoscopic viewing image generation method of the present invention may further include the step of selectively generating either one of the stereoscopic viewing image and the non-stereoscopic viewing image based on the predetermined output image selection condition and outputting the selectively generated image.

Further, the stereoscopic viewing image generation program recorded on a non-transitory computer readable recording medium of the present invention may be a program that causes a computer to perform either one of the embodiments described above.

The term "an output image selection condition" refers to a condition that defines whether to output either one of the stereoscopic viewing image and the non-stereoscopic viewing image or both to each output destination device, which may include a condition that defines neither the stereoscopic viewing image nor the non-stereoscopic viewing image is outputted.

More specifically, the "output image selection condition" may be defined according to the output destination of the stereoscopic viewing image or the non-stereoscopic viewing image. For example, the output image selection condition may be a condition that, if the output destination device is a device capable of displaying the stereoscopic viewing image, causes the stereoscopic viewing image to be outputted, while, if the output destination device is an image storage device for storing a medical image, causes the non-stereoscopic viewing image to be outputted. Further, the output image selection condition may be a condition that, if the output destination device is a device capable of presenting the stereoscopic viewing image, causes the stereoscopic viewing image to be outputted, while, if the output destination device is a device not capable of presenting the stereoscopic viewing image, causes the non-stereoscopic viewing image to be outputted. A specific example of device not capable of presenting the stereoscopic viewing image is a device that outputs a hard copy of a medical image.

The output destination device of the selective output means may be a device capable of selectively presenting a stereoscopic display based on the stereoscopic viewing image and a non-stereoscopic display based on the non-stereoscopic viewing image, and the output image selection condition may be a condition that, when an operation of an input means for specifying a desired position in the stereoscopic viewing image stereoscopically displayed on the display device is detected, causes the non-stereoscopic viewing image to be outputted. In this case, the display device may be a device further capable of displaying a screen in which stereoscopic display and non-stereoscopic display are presented in a mixed manner. Still further, a cross-sectional image for non-stereoscopically viewing a given cross-section of the subject may be generated based on the three-dimensional medical image and a screen in which the cross-sectional image and the stereoscopic viewing image or the non-stereoscopic viewing image are presented in a mixed manner may be displayed on the display device.

In the present invention, the stereoscopic viewing image may be displayed on a display device capable of performing stereoscopic display and, when an operation of an input means for specifying a desired position in the stereoscopic viewing image stereoscopically displayed on the display device is performed, the specified position may be identified using the non-stereoscopic viewing image.

According to the present invention, not only a stereoscopic viewing image but also a non-stereoscopic viewing image equivalent to the stereoscopic viewing image are generated using a three-dimensional medical image as input and based on an image generation condition of the stereoscopic viewing image, so that the invention may respond flexibly and appropriately to the case where stereoscopic output is inappropriate or not required.

In the present invention, a three-dimensional medical image is used as input, so that a non-stereoscopic viewing image equivalent to a stereoscopic viewing image may be generated easily and flexibly without requiring image recapturing.

If an arrangement is adopted in which a stereoscopic viewing image and a non-stereoscopic viewing image are selectively outputted based on a predetermined output image selection condition, the stereoscopic viewing image may be outputted more flexibly and appropriately according to the situation and intended use.

As a specific example of selective output, if the output destination device is capable of presenting a stereoscopic viewing image, a stereoscopic viewing image is outputted while, if the output destination device is not capable of presenting a stereoscopic viewing image, a non-stereoscopic viewing image is outputted, the stereoscopic viewing image may be outputted only to a device capable of or required for performing stereoscopic display, resulting in an improved connection compatibility with an output device.

Further, if an arrangement is adopted in which, when an operation of an input means involving specification of a desired position in a stereoscopic viewing image stereoscopically displayed on a display device is detected, a non-stereoscopic viewing image is outputted, then unpleasant feeling due to a material difference of visual line from the visual line for viewing the stereoscopic image, such as the case in which either one of the parallax images is outputted for performing the operation is eliminated or the case in which a position different from the position desired by the user is specified in the operation described above is prevented, whereby the operability is improved.

BRIEF DESCRIPTION OF THE DRAWINGS

FIG. 6 illustrates, by way of example, the structure and contents of an output image selection condition table.

FIG. 10 illustrates, by way of example, a screen structure displayed on a stereoscopic viewing support display unit.

DESCRIPTION OF THE PREFERRED EMBODIMENTS

Hereinafter, a medical image diagnosis system that employs a stereoscopic viewing image generation apparatus according to an embodiment of the present invention will be described.

Figure 1:
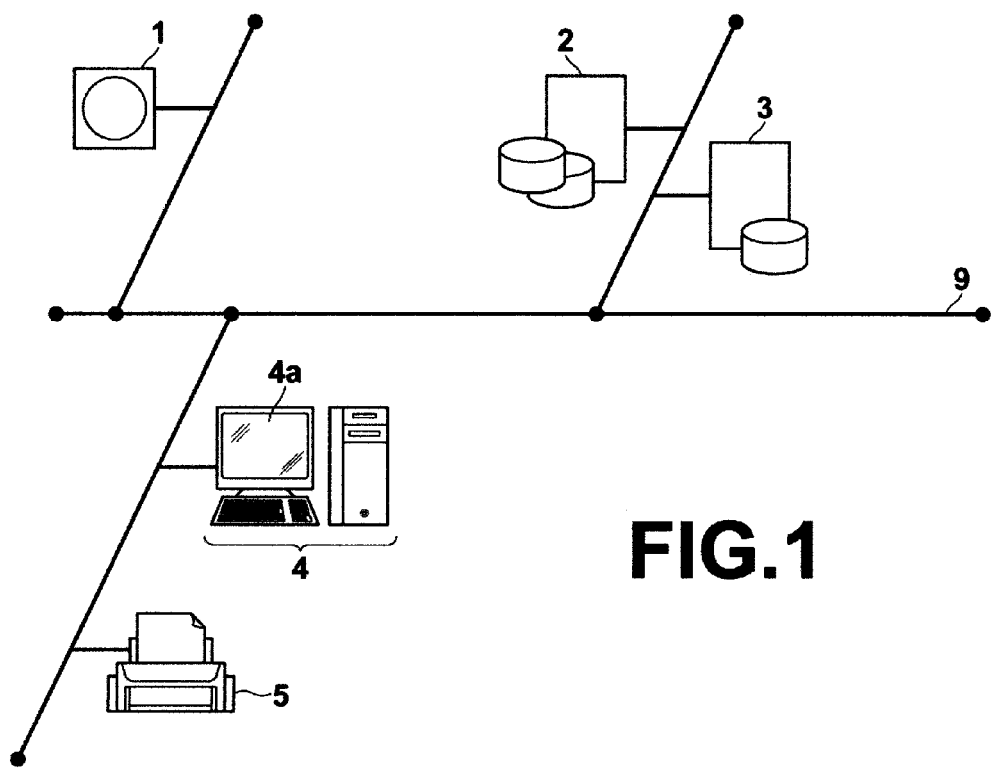
FIG. 1 is a schematic configuration diagram of a medical image diagnosis system that employs a stereoscopic viewing image generation apparatus according to an embodiment of the present invention.

FIG. 1 is a hardware configuration diagram of the medical image diagnosis system, illustrating an overview thereof. As shown in FIG. 1, the system includes modality 1, image storage server 2, radiology report server 3, image processing workstation 4, and printer 5 communicatably connected to each other via network 9.

Modality 1 includes an apparatus that images an inspection target region of a subject to generate image data representing a three-dimensional medical image of the region and outputs the image data by attaching auxiliary information defined in DICOM (Digital Imaging and Communication in Medicine) standard as image information. Specific examples of the apparatus include, for example, CT, MRI, and the like.

Image storage server 2 is a computer for storing medical image data, in a database, obtained by modality 1 and image data of a medical image generated by image processing in image processing workstation 4 and managing them, and includes a large capacity external memory unit and database management software (e.g., Object Relational Database (ORDB)). In addition, image storage server 2 searches the data base in response to a retrieval request from image processing workstation 4 and sends retrieved image data to the image processing workstation 4 that has made the request.

Radiology report server 3 is a computer for storing data of radiology reports, in a database, generated by image processing workstation 4 and managing them. In addition, radiology report server 3 searches the data base in response to a retrieval request from image processing workstation 4, the other workstation, or the like (not shown) and sends retrieved image data to the image processing workstation 4 that has made the request. Note that the radiology report includes a finding made by the radiology reader for the radiology reading target image and appended images, including the image in which the finding is appearing, a reference image, and the like.

Image processing workstation 4 is a computer provided with known hardware devices, such as a CPU, a main storage unit, an auxiliary storage unit, an input/output interface, a communication interface, input devices (pointing device, keyboard, and the like), a data bus, and the like. In the present embodiment, in particular, workstation 4 includes stereoscopic viewing support display unit 4a. Image processing workstation 4 has a known operating system and application software installed thereon. In the present embodiment, an image retrieval and acquisition application for obtaining medical image data from image storage server 2 in collaboration with a known ordering system, an image processing application for performing various image processing, a radiology report application for generating/editing a radiology report and obtaining a radiology report from radiology report server 3, an application for performing the stereoscopic viewing image generation of the present invention are installed, as the application software. The application software may be installed from a recording medium, such as a CD-ROM or the like or may be downloaded from a storage server and installed. Various types of processing described above are performed in image processing workstation 4 by executing these applications.

Figure 4:
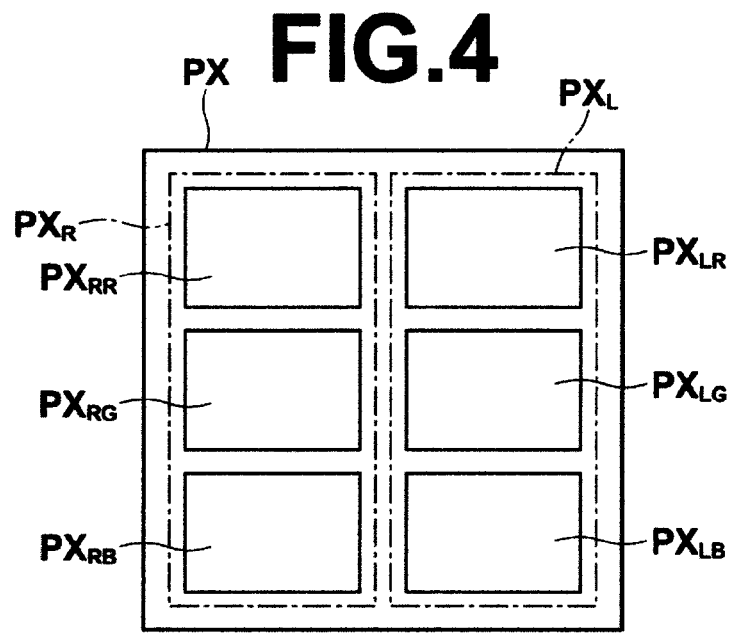
FIG. 4 schematically illustrates a structure of one display pixel of a stereoscopic viewing support display unit.

In the present embodiment, as stereoscopic viewing support display unit 4a, a display unit capable of performing mixed display of stereoscopic display and non-stereoscopic display is used (for details, refer to "High Quality 2D/3D Display" by S. Uehara and K. Shigemura, NEC Technical Journal, NEC Corporation, Japan, April 2009, Vol. 62, No. 2, pp. 48-52, Internet (Date of Retrieval: Jan. 14, 2010), URL: http://www.nec.co.jp/techrep/ja/journal/g09/n02/090210.pdf). More specifically, one display pixel PX of stereoscopic viewing support display unit 4a includes right eye pixel $PX_R$ disposed on the left and left eye pixel $PX_L$ disposed on the right, as schematically shown in FIG. 4. Pixels $PX_R$ and $PX_L$ are divided into red display areas $PX_{RR}$ and $PX_{LR}$, green display areas $PX_{RG}$ and $PX_{LG}$, and blue display areas $PX_{RB}$ and $PX_{LB}$ respectively by a color filter striped in a transverse direction. Stereoscopic display support display unit 4a has a combined structure of a matrix of pixels PX and an optical element, such as lenticular lens, parallax barrier, or the like. A parallax image for right eye is displayed on the matrix of right eye pixels $PX_R$ and a parallax image for left eye is displayed on the matrix of left eye pixels $PX_L$, thereby realizing a stereoscopic display viewable by the naked eyes of the user. Further, stereoscopic viewing support display unit 4a is capable of performing non-stereoscopic display by displaying the same image on both of the matrix of right eye pixels $PX_R$ and the matrix of left eye pixels $PX_L$. Consequently, a mixed display of stereoscopic and non-stereoscopic displays can be realized by displaying parallax images on the pixels of respective eyes in a portion of the display screen while displaying the same image on the pixels of respective eyes in the other portion of the display screen.

The storage format of image data and communication between each component of the system are based on the DICOM protocol or the like.

Figure 2:
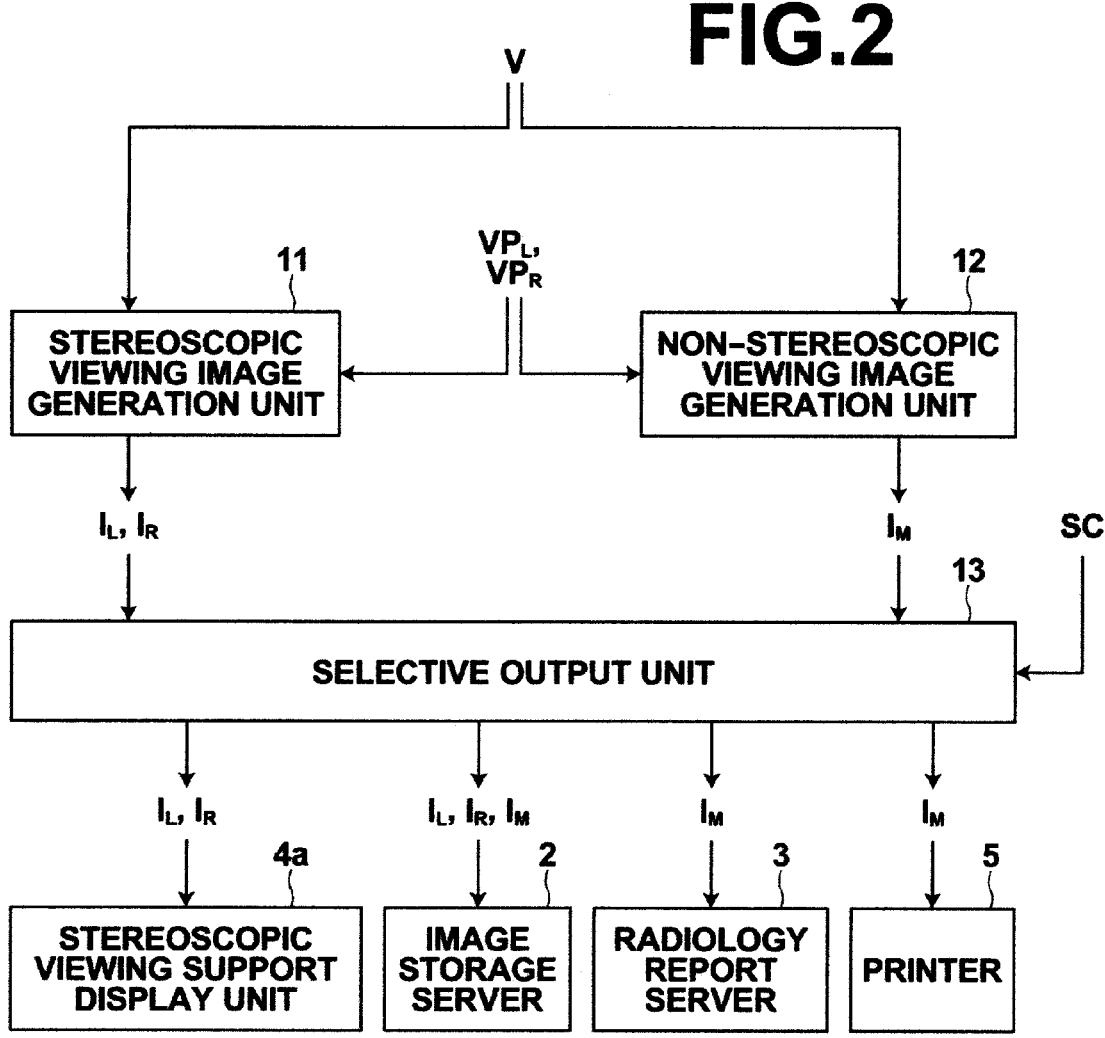
FIG. 2 is a block diagram schematically illustrating a configuration and a process flow for realizing a stereoscopic viewing image generation function in a first embodiment of the present invention.

FIG. 2 is a block diagram, illustrating a portion of the function of image processing workstation 4 relevant to the stereoscopic viewing image generation process according to the first embodiment of the present invention. As shown in FIG. 2, the stereoscopic viewing image generation processing according to the first embodiment of the present invention is realized by stereoscopic viewing image generation unit 11, non-stereoscopic viewing image generation unit 12, and selective output unit 13. In FIG. 2, the three-dimensional medical image V, left eye viewpoint position $VP_L$, right eye viewpoint position $VP_R$, left eye parallax image $I_L$, right eye parallax image $I_R$, non-stereoscopic viewing image $I_M$, and output image selection condition table SC are data written into and read out from a predetermined memory area of image processing workstation 4 by each of the processing units described above.

Figure 3:
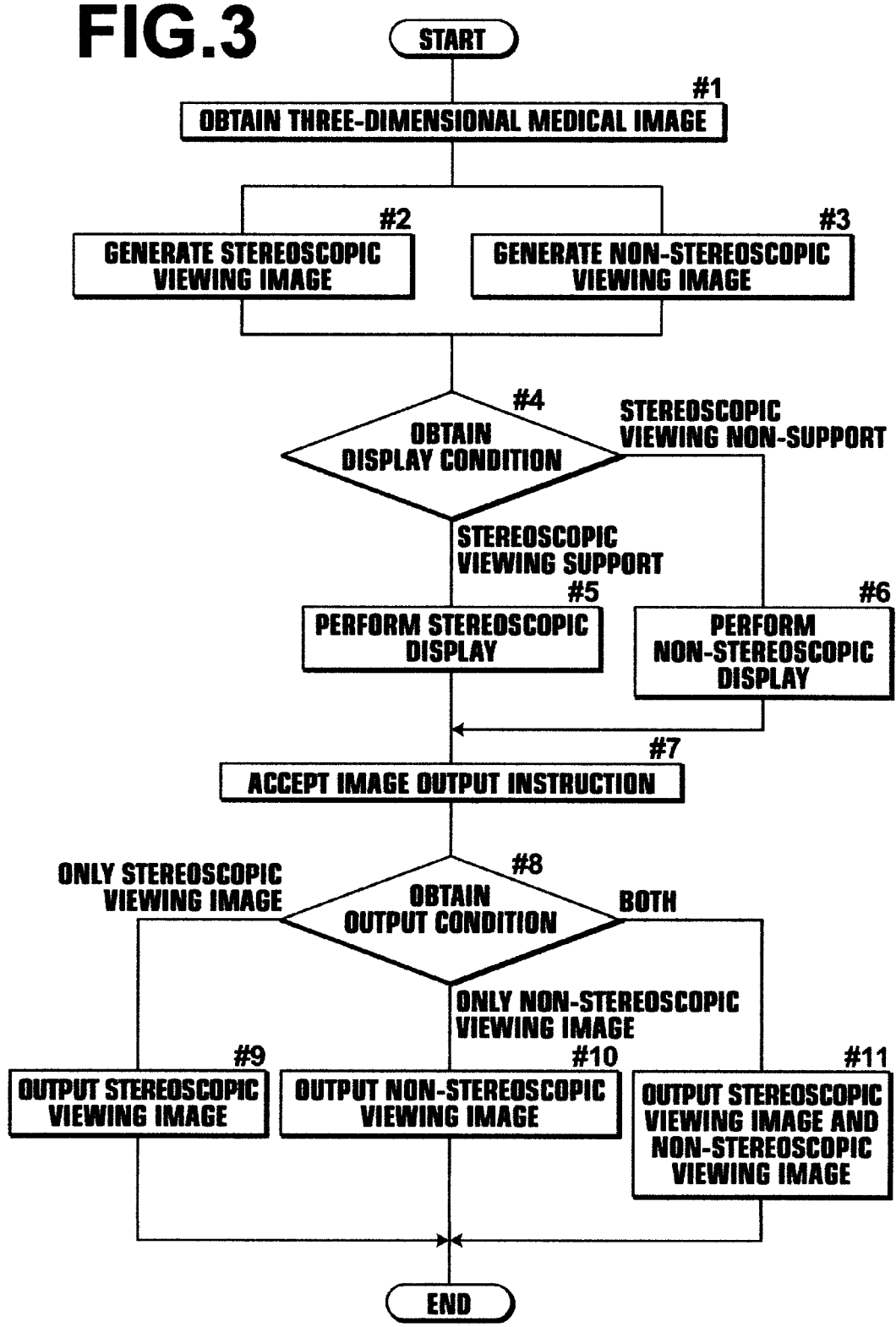
FIG. 3 is a flowchart illustrating a process flow for generating a stereoscopic viewing image in the first embodiment of the present invention.

FIG. 3 is a flowchart illustrating a flow of user operation, calculation processing, display processing, and the like performed under the execution of stereoscopic viewing image generation software according to the first embodiment of the present invention. First, image processing workstation 4 obtains image data of a processing target three-dimensional medical image V from image storage server 2 through image retrieval and acquisition processing of a known image retrieval system or of a known ordering system (#1).

Then, stereoscopic viewing image generation unit 11 generates left eye parallax image $I_L$ and right eye parallax image $I_R$ for implementing a stereoscopic output based on the three-dimensional medical image V, left eye viewpoint position $VP_L$, and right eye viewpoint position $VP_R$ (#2), and non-stereoscopic viewing image generation unit 12 determines one viewpoint equivalent to the stereoscopic output from the left eye viewpoint position $VP_L$ and right eye viewpoint position $VP_R$ and generates a non-stereoscopic viewing image $I_M$ for implementing a non-stereoscopic output equivalent to the stereoscopic output based on the three-dimensional medical image V (#3).

Selective output unit 13 refers to an output image selection condition table SC and obtains information that indicates whether or not the display unit of image processing workstation 4, which is the destination display unit, supports stereoscopic viewing (#4). If the destination unit supports stereoscopic viewing (#4: stereoscopic viewing support), as in the present embodiment, selective output unit 13 outputs the left eye parallax image $I_L$ and right eye parallax image $I_R$ to the destination display unit, and the display unit performs a stereoscopic display based on the left eye parallax image $I_L$ and right eye parallax image $I_R$ (#5). If the destination display unit does not support stereoscopic display (#4: stereoscopic viewing non-support), selective output unit 13 outputs the non-stereoscopic viewing image $I_M$ to the destination display unit, and the display unit displays the non-stereoscopic viewing image $I_M$ (#6).

After observing the image displayed on the display unit of image processing workstation 4, if the user specifies a destination for outputting (storing, printing) the observed image (#7), selective output unit 13 refers to the output image selection condition table SC and determines whether to output either the pair of left eye parallax image $I_L$ and right eye parallax image $I_R$ for stereoscopic viewing or the non-stereoscopic viewing image $I_M$, or to output the both to the image output destination (#8). If stereoscopic viewing image is set in the output image selection condition table SC as the output target image (#8: stereoscopic viewing image only), selective output unit 13 outputs the left eye parallax image $I_L$ and right eye parallax image $I_R$ to the output destination (#9). If non-stereoscopic viewing image is set in the table as the output target image (#8: non-stereoscopic viewing image only), selective output unit 13 outputs the non-stereoscopic viewing image $I_M$ to the output destination (#10), while if both of stereoscopic viewing image and non-stereoscopic viewing image are set in the table (#8: both), selective output unit 13 outputs the left eye parallax image $I_L$, right eye parallax image $I_R$, and non-stereoscopic viewing image $I_M$ to the output destination (#11).

Processing performed in each processing unit will now be described in detail.

Figure 5:
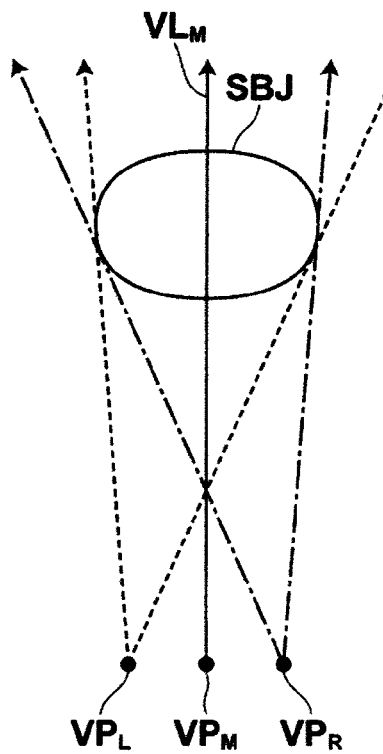
FIG. 5 illustrates, in plan, a positional relationship between a subject in a three-dimensional medical image, viewpoints of left and right eye parallax images, and a single viewpoint equivalent to the viewpoints.

Stereoscopic viewing image generation unit 11 generates left eye parallax image $I_L$ and right eye parallax image $I_R$ based on a three-dimensional medical image V, left eye viewpoint position $VP_L$, and right eye viewpoint position $VP_R$. FIG. 5 schematically illustrates the positional relationship between a subject in a three-dimensional medical image and viewpoints of left and right eyes. As illustrated in FIG. 5, stereoscopic viewing image generation unit 11 generates, by volume rendering, left eye parallax image $I_L$ by projecting pixels on each visual line connecting between the left eye viewpoint position $VP_L$ and a subject SBJ and right eye parallax image $I_R$ by projecting pixels on each visual line connecting between the right eye viewpoint position $VP_R$ and the subject SBJ. Here, the left eye viewpoint position $VP_L$ and right eye viewpoint position $VP_R$ may be preset as startup parameters of the program, or a user interface (e.g., setting screen like that shown in FIG. 5) may be provided for setting each of the viewpoint positions $VP_L$, $VP_R$ to allow the user to manually set each of the viewpoint positions $VP_L$, $VP_R$ or to allow preset viewpoint positions to be corrected in order to compensate for the difference in left/right parallax between individuals. FIG. 5 illustrates the central projection from each of the viewpoint positions $VP_L$, $VP_R$, but each of the parallax images $I_L$, $I_R$ may be generated by a parallel projection in the direction of the visual line connecting between each of viewpoint positions $VP_L$, $VP_R$ and the center of the subject SBJ, assuming that the each viewpoint is at infinite distance from the subject SBJ in each visual direction.

Based on the left eye viewpoint position $VP_L$ and right eye viewpoint position $VP_L$, non-stereoscopic viewing image generation unit 12 first determines one viewpoint position (equivalent viewpoint position) which is equivalent to the case in which the subject is viewed by positioning each of left and right eyes to each eye viewpoint position. More specifically, the midpoint of the line segment connecting between the left eye viewpoint position $VP_L$ and right eye viewpoint position $VP_R$ is determined to be an equivalent viewpoint position $VP_M$ of a non-stereoscopic viewing image, as illustrated in FIG. 5. Here, the equivalent viewpoint position $VP_M$ may be the other position at equidistance from each of the left and right viewpoint positions or a weighted average position between the left eye viewpoint position $VP_L$ and right eye viewpoint position $VP_R$, i.e., a position that internally divides the line segment connecting between left and right viewpoints at a predetermined ratio (e.g., 3:2) in view of the difference in left/right parallax between individuals. Further, for example, the equivalent viewpoint position $VP_M$ may be determined on an arc centered on the gravity center of the subject SBJ and passing through the left and right viewpoint positions, instead of determining it on the line segment connecting between left and right viewpoints.

Next, non-stereoscopic viewing image generation unit 12 generates, by volume rendering, a non-stereoscopic viewing image $I_M$ by projecting pixels on each visual line connecting between the equivalent viewpoint position $VP_M$ and subject SBJ. As for the specific projection method used in non-stereoscopic viewing image generation unit 12 (central projection or parallel projection), the same method as that used in stereoscopic viewing image generation unit 11 may be used.

Here, an arrangement may be adopted in which processing performed in stereoscopic viewing image generation unit 11 and non-stereoscopic viewing image generation unit 12 for generating, by volume rendering, an image by projecting pixels on each visual line connecting a preset viewpoint position and a subject is configured as a common module and a processing module for determining the equivalent viewpoint position $VP_M$ and visual direction is separately provided. Then, a pair of parallax images $I_L$, $I_R$ for stereoscopic viewing or a non-stereoscopic viewing image $I_M$ is generated by the common module by receiving viewpoint position information according to the generation target image as processing parameter.

Selective output unit 13 selectively outputs the left and right eye parallax images $I_L$, $I_R$ or the non-stereoscopic viewing image $I_M$.

FIG. 6 illustrates an example of the structure and contents of the output image selection condition table SC. As shown in FIG. 6, the output image selection condition table SC defines whether or not to output (Y: output, N: not output) the stereoscopic viewing image (left and right eye parallax images $I_L$, $I_R$) and the non-stereoscopic viewing image with respect to each output destination device. That is, in FIG. 5, selective output unit 13 is set to output left and right eye parallax images $I_L$, $I_R$ to stereoscopic viewing support display unit 4a, only a non-stereoscopic viewing image $I_M$ to a stereoscopic viewing non-support display unit, radiology report server 3, and printer 5, and the left and right eye parallax images $I_L$, $I_R$ and non-stereoscopic viewing image $I_M$ to image storage server 2. Selective output unit 13 refers to the output image selection condition table SC based on the information of output destination device given as a startup parameter or by user specification to identify the type of image to be outputted to the output destination device and outputs the identified image or images.

When the left and right eye parallax images $I_L$, $I_R$ are outputted to stereoscopic viewing support display unit 4a by selective output unit 13, the left eye parallax image $I_L$ is displayed on the matrix of left eye pixels $PX_L$ while the right eye parallax image $I_R$ is displayed on the matrix of right eye pixels $PX_R$ in stereoscopic viewing support display unit 4a.

As described above, in the first embodiment of the present invention, parallax images $I_L$, $I_R$ generated by stereoscopic viewing image generation unit 11 using a three-dimensional image V as input and non-stereoscopic viewing image $I_M$ generated by non-stereoscopic viewing image generation unit 12 using the three-dimensional image V as input are selectively outputted by selective output unit 13 based on an output image selection condition table SC. This allows a stereoscopic viewing image or a non-stereoscopic viewing image to be outputted flexibly and appropriately according to the intended use.

More specifically, the output image selection condition table SC is set to cause a stereoscopic viewing image to be outputted to stereoscopic viewing support display unit 4a capable of displaying a stereoscopic image and a non-stereoscopic viewing image to be outputted to a stereoscopic viewing non-support display unit not capable of displaying a stereoscopic image. This allows an appropriate image to be outputted according to the type of the display unit connected to image processing workstation 4. Further, when output image selection condition table SC is set such that an appended image for non-stereoscopic viewing is outputted from radiology report server 3 in view of the fact that a radiology report is referenced not only by image processing workstation 4 having stereoscopic viewing support display unit 4a connected thereto but also by other workstations, the radiology report can be referenced by an ordinary display unit without using a special display unit such as stereoscopic viewing support display unit 4a. Likewise, if stereoscopic viewing is not assumed when a radiology report is outputted in hard copy form on a paper or film by printer 5, an image appropriate for observation may be outputted from printer 5 by setting the output image selection condition table SC such that an image for non-stereoscopic viewing is outputted from printer 5. In the mean time, if output image selection condition table SC is set such that parallax images $I_L$, $I_R$ and non-stereoscopic viewing image $I_M$ are outputted from image storage server 2, an appropriate image can be provided according to each of retrieval requests from various types of workstations. The setting of output image selection condition table SC described above is only an example, and the table SC may be set appropriately according to the intended use of the image, system configuration, and the like, such as for example, causing image storage server 2 to output only the non-stereoscopic viewing image $I_M$.

Further, a three-dimensional image V is used as input, so that a non-stereoscopic viewing image $I_M$ equivalent to a stereoscopic viewing image can be generated easily and flexibly without requiring image recapturing.

Still further, the non-stereoscopic viewing image $I_M$ is an image of a subject viewed from a single viewpoint equivalent to the case in which the subject is viewed from a left eye viewpoint position and a right eye viewpoint position, so that unpleasant feeling due to a material difference in visual line between a stereoscopic output based on the left and right eye parallax images $I_L$, $I_R$ and a non-stereoscopic output based on the non-stereoscopic viewing image $I_M$ may be eliminated.

Figure 7A:
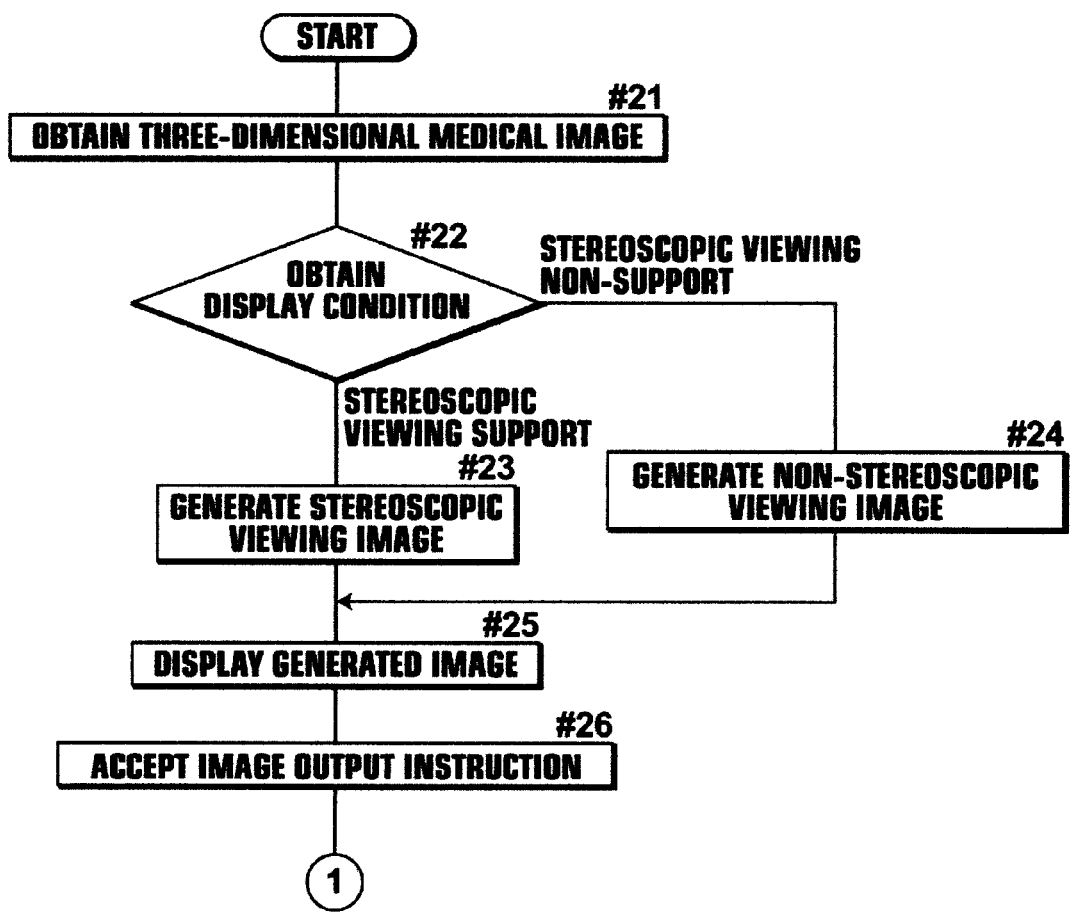
FIG. 7A is a flowchart illustrating a process flow for generating a stereoscopic viewing image in a modification of the first embodiment of the present invention (former half).
Figure 7B:
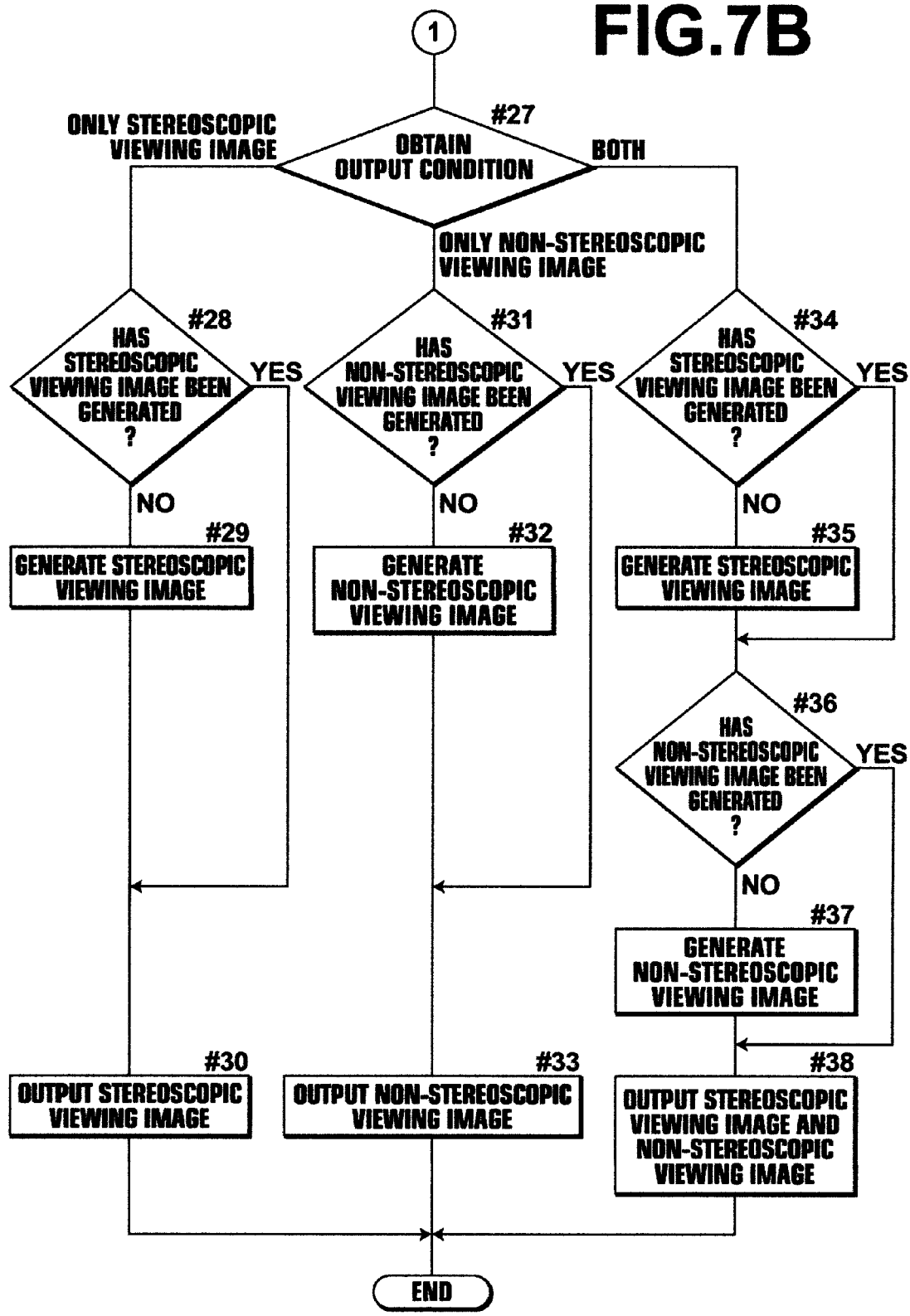
FIG. 7B is a flowchart illustrating a process flow for generating a stereoscopic viewing image in a modification of the first embodiment of the present invention (latter half).

In the embodiment described above, left and right eye parallax images $I_L$, $I_R$ for stereoscopic viewing and non-stereoscopic viewing image $I_M$ are generated, but they may be generated when outputted as required, as shown in the flowchart of FIGS. 7A, 7B.

That is, after image data of a processing target three-dimensional medical image V is obtained in image processing workstation 4 (#21), selective output unit 13 refers to an output image selection condition table SC and obtains information that indicates whether or not the display unit of image processing workstation 4 supports stereoscopic viewing. If the destination unit supports stereoscopic viewing (#22: stereoscopic viewing support), stereoscopic viewing image generation unit 11 is caused to generate left eye parallax image $I_L$ and right eye parallax image $I_R$ (#23), while if the destination unit does not support stereoscopic viewing (#22: stereoscopic viewing non-support) non-stereoscopic viewing image generation unit 12 is caused to generate a non-stereoscopic viewing image $I_M$ (#24), and the generated image is outputted and displayed on the display unit (#25).

After observing the displayed image, if the user specifies a destination for outputting (storing, printing) the observed image (#26), selective output unit 13 refers to the output image selection condition table SC and identifies the type of image to be outputted to the specified output destination device (#27). If stereoscopic viewing image is set in the output image selection condition table SC as the output target image (#27: stereoscopic viewing image only), and if the left eye parallax image $I_L$ and right eye parallax image $I_R$ have not been generated yet (#28: NO), selective output unit 13 causes stereoscopic viewing image generation unit 11 to generate the left eye parallax image $I_L$ and right eye parallax image $I_R$ (#29) and outputs the left eye parallax image $I_L$ and right eye parallax image $I_R$ generated in step #23 (when #28:YES) or in step #29 to the output destination device (#30). If non-stereoscopic viewing image is set in the output image selection condition table SC as the output target image (#27: non-stereoscopic viewing image only), and if the non-stereoscopic viewing image $I_M$ has not been generated yet (#31: NO), selective output unit 13 causes non-stereoscopic viewing image generation unit 12 to generate the non-stereoscopic viewing image $I_M$ (#32) and outputs the non-stereoscopic viewing image $I_M$ generated in step #24 (when #31:YES) or in step #32 to the output destination device (#33). If both of the stereoscopic viewing image and non-stereoscopic viewing image are set as the output target image (#27: Both), and if the left eye parallax image $I_L$ and right eye parallax image $I_R$ have not been generated yet (#34: NO), selective output unit 13 causes stereoscopic viewing image generation unit 11 to generate the left eye parallax image $I_L$ and right eye parallax image $I_R$ (#35). Further, if the non-stereoscopic viewing image $I_M$ has not been generated yet (#36: NO), selective output unit 13 causes non-stereoscopic viewing image generation unit 12 to generate the non-stereoscopic viewing image $I_M$ (#37) and outputs the left eye parallax image $I_L$ and right eye parallax image $I_R$ generated in step #23 (when #34: YES) or in step #35 and the non-stereoscopic viewing image $I_M$ generated in step #24 (when #36: YES) or in step #37 to the output destination device (#38).

As described above, if a stereoscopic viewing image and/or a non-stereoscopic viewing image is caused to be generated as required by selective output unit 13, the processing efficiency of image processing workstation 4 is improved. It is particularly effective when a change operation for the viewpoint position or the like is allowed for an image displayed on the display unit of image processing workstation 4 in step #25, the display target image is regenerated by stereoscopic viewing image generation unit 11 or non-stereoscopic viewing image generation unit 12 according to the operation, and the image displayed on the display unit is updated. That is, in the flowchart of FIG. 3, if, for example, the viewpoint position is changed for the stereoscopically displayed image in step #5, then not only the parallax images $I_L$, $I_R$ for stereoscopic viewing but also the non-stereoscopic viewing image $I_M$ already generated in step #3 as a set are to be regenerated, whereby the non-stereoscopic viewing image $I_M$ generated in step #3 is wasted. In contrast, in the flowchart of FIGS. 7A, 7B, even if the change operation for the viewpoint position is repeated at the time point of step #25, the parallax images $I_L$, $I_R$ for stereoscopic viewing and non-stereoscopic viewing image $I_M$ may be generated once at the time point of #26, resulting in improved processing efficiency.

Next, an embodiment in which switching between a stereoscopic display and a non-stereoscopic display is performed on stereoscopic viewing support display unit 4a connected to image processing workstation 4 in the medical image diagnosis system shown in FIG. 1 will be described, as a second embodiment of the present invention.

Figure 8:
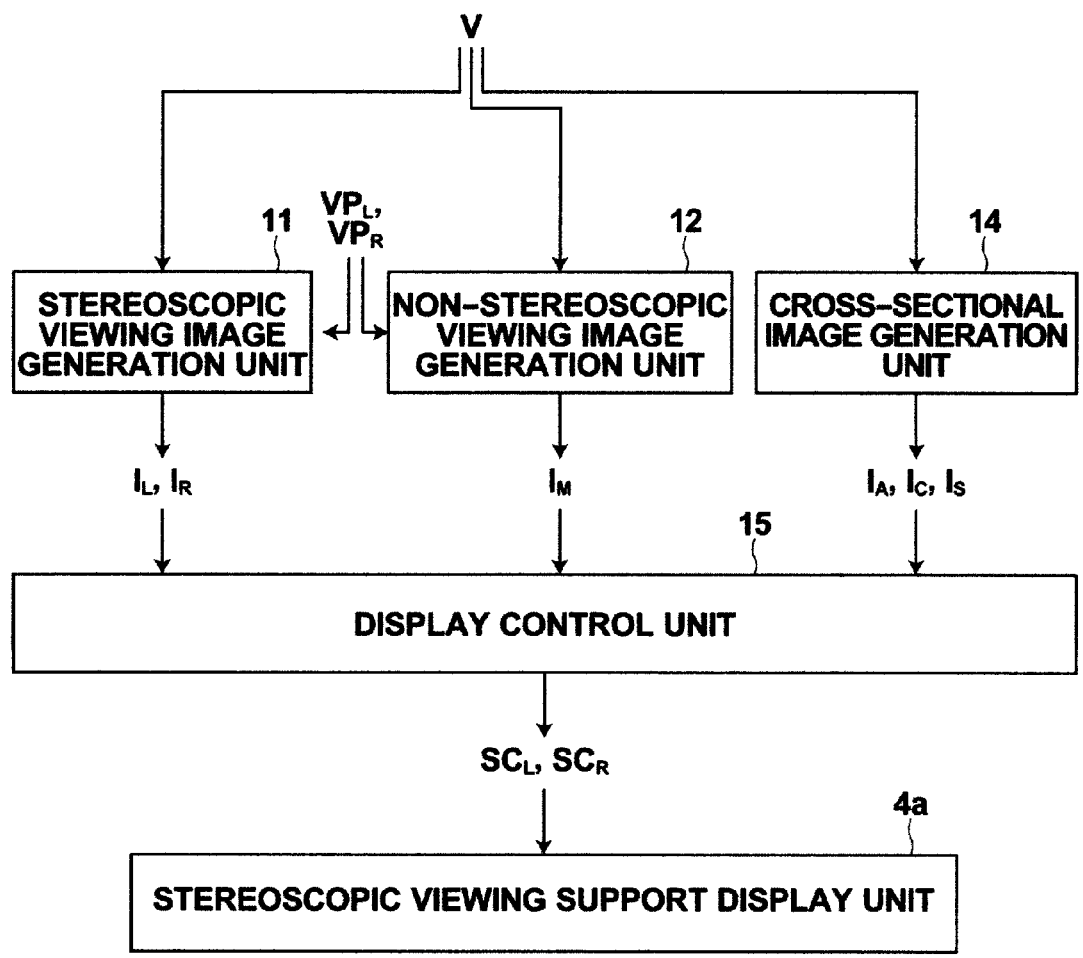
FIG. 8 is a block diagram, schematically illustrating a configuration and a process flow for realizing a stereoscopic viewing image generation function in a second embodiment of the present invention.

FIG. 8 is a block diagram illustrating a portion of the function of image processing workstation 4 relevant to the stereoscopic viewing image generation processing according to the second embodiment of the present invention. As shown in FIG. 8, stereoscopic viewing image generation processing of the second embodiment of the present invention is achieved realized by stereoscopic viewing image generation unit 11, non-stereoscopic viewing image generation unit 12, cross-sectional image generation unit 14, and display control unit 15. In FIG. 8, the three-dimensional medical image V, left eye viewpoint position $VP_L$, right eye viewpoint position $VP_R$, left eye parallax image $I_L$, right eye parallax image $I_R$, non-stereoscopic viewing image $I_M$, axial cross-sectional image $I_A$/coronal cross-sectional image $I_C$, sagittal cross-sectional image $I_S$, (three cross-sectional images are hereinafter collectively referred to as three orthogonal cross-sectional images unless any distinction is specifically required), left eye display screen $SC_L$, and right eye display screen $SC_R$ are data written into and read out from a predetermined memory area of image processing workstation 4 by each of the processing units described above.

Figure 9:
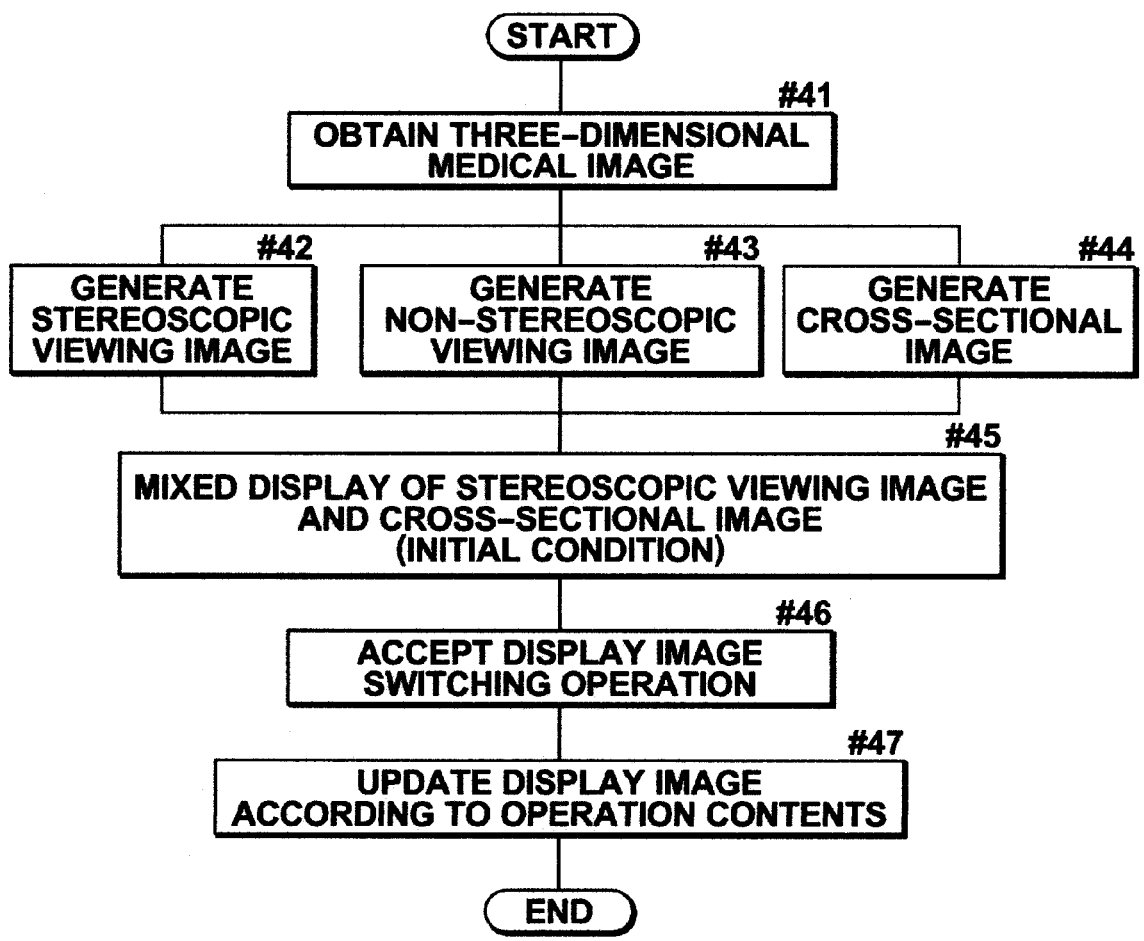
FIG. 9 is a flowchart illustrating a process flow for generating a stereoscopic viewing image in the second embodiment of the present invention.

FIG. 9 is a flowchart illustrating a flow of user operation, calculation processing, display processing, and the like performed under the execution of stereoscopic viewing image generation software according to the second embodiment of the present invention.

First, image processing workstation 4 obtains image data of a processing target three-dimensional medical image V from image storage server 2 through image retrieval and acquisition processing of a known image retrieval system or of a known ordering system (#41).

Then, stereoscopic viewing image generation unit 11 generates left eye parallax image $I_L$ and right eye parallax image $I_R$ for implementing a stereoscopic output based on the three-dimensional medical image V, left eye viewpoint position $VP_L$, and right eye viewpoint position $VP_R$ (#42), and non-stereoscopic viewing image generation unit 12 determines one viewpoint equivalent to the stereoscopic output from the left eye viewpoint position $VP_L$ and right eye viewpoint position $VP_R$ and generates a non-stereoscopic viewing image $I_N$ for implementing a non-stereoscopic output equivalent to the stereoscopic output based on the three-dimensional medical image V (#43). In addition, cross-sectional image generation unit 14 generates three orthogonal cross-sectional images $I_A$, $I_C$, $I_S$ for non-stereoscopically viewing three cross-sections (axial, coronal, and sagittal cross-sections) intersecting at a given point of a subject at right angles (#44).

Display control unit 15 generates a left eye display screen $SC_L$ that includes the left eye parallax image $I_L$ and three orthogonal cross-sectional images $I_A$, $I_C$, $I_S$, and a right eye display screen $SC_R$ that includes the right eye parallax image $I_R$ and three orthogonal cross-sectional images $I_A$, $I_C$/$I_S$ based on a predetermined display protocol (initial display condition) and outputs the left and right eye display screens $SC_L$, $SC_R$ to stereoscopic viewing support display unit 4a. This causes stereoscopic viewing support display unit 4a to perform mixed display of stereoscopic display based on the left eye parallax image $I_L$ and right eye parallax image $I_R$ and non-stereoscopic display of the three orthogonal cross-sectional images (#45, FIGS. 11A to 11C).

Here, if an instruction is given by the user to perform switching between the stereoscopic display and non-stereoscopic display or to perform switching of images to be displayed by operating the keyboard or pointing device of image processing workstation 4 (#46), display control unit 15 reconstructs the left and right eye display screens $SC_L$, $SC_R$ according to the operation contents and outputs the reconstructed display screens $SC_L$, $SC_R$ to stereoscopic viewing support display unit 4a, whereby the display on stereoscopic viewing support display unit 4a is updated (#47).

Processing performed in each processing unit will now be described in detail. Processing performed in stereoscopic viewing image generation unit 11 and non-stereoscopic viewing image generation unit 12 is identical to that of the first embodiment.

Based on the three-dimensional medical image V and position information of a given point of a subject, cross-sectional image generation unit 14 generates cross-sectional images $I_A$, $I_C$, $I_S$ of axial, coronal, and sagittal three orthogonal cross-sections passing the given point by a known MPR technique. The point in the subject serving as the basis of the position of cross-sections may be preset as a startup parameter of the program or the like, or a user interface may be provided for setting the position of the cross-sections to allow the user to manually set the position or to allow the preset position to be corrected.

Display control unit 15 appropriately selects a display target image from left and right eye parallax images $I_L$, $I_R$, and three orthogonal cross-sectional images $I_A$, $I_C$, $I_s$ according to a given display condition to generate left and right eye display screens $SC_L$, $SC_R$ and outputs the generated display screens $SC_L$, $SC_R$ to stereoscopic viewing support display unit 4a. That is, display control unit 15 is one example implementation of the selective output means of the present invention and the display condition corresponds to an output image selection condition. The display condition may be given as a startup parameter of the program or by a manual operation of the user at a user interface (user interface area 22 in FIG. 10) to be described later.

FIG. 10 schematically illustrates, by way of example, a structure of the display screen which is common to display screens $SC_L$, $SC_R$. As shown in FIG. 10, left and right eye display screens $SC_L$, $SC_R$ include image display area 21 and user interface area 22. Image display area 21 includes sub-areas 21a, 21b, 21c, 21d to which each image is allocated, whereby four images can be displayed arranged in a 2×2 matrix. In the mean time, user interface area 22 includes a user interface for performing display image switching, image editing, and the like. More specifically, as a user interface for selecting/switching a display image, checkboxes 22a are provided for selecting display or non-display of three orthogonal cross-sectional images $I_A$, $I_C$, $I_S$ and a volume rendering image, i.e., left and right eye parallax images $I_L$, $I_R$ for stereoscopic viewing and non-stereoscopic viewing image $I_M$. Further, checkbox 22b for selecting whether or not to stereoscopically view the volume rendering image, radio buttons 22c for changing the layout of image display area 21, annotation buttons 22d for inserting an arrow, a mark, and a comment, and image editing buttons 22e for editing an image, such as cutting in the visual line direction, enlarging an area of attention, and the like are also provided.

Figure 11A:
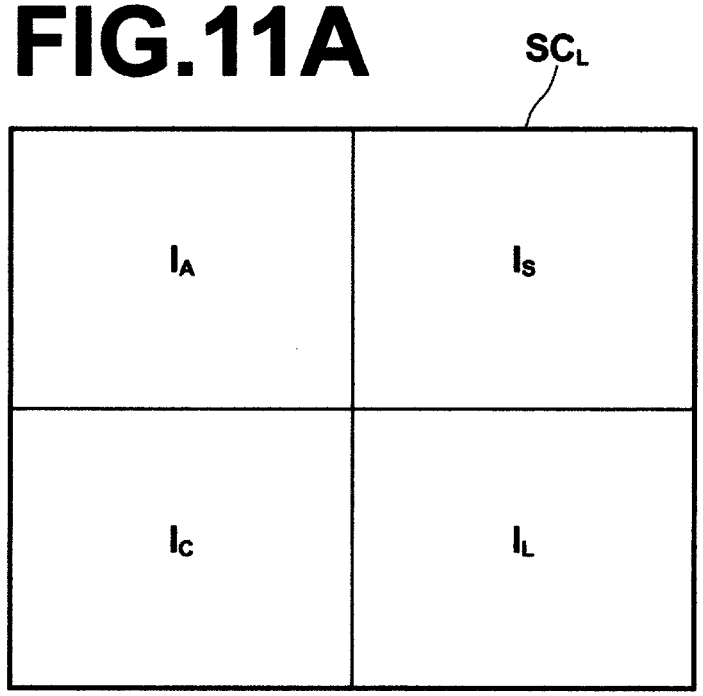
FIG. 11A illustrates, by way of example, a layout of left eye parallax image and three orthogonal cross-sectional images in a left eye display screen.
Figure 11B:
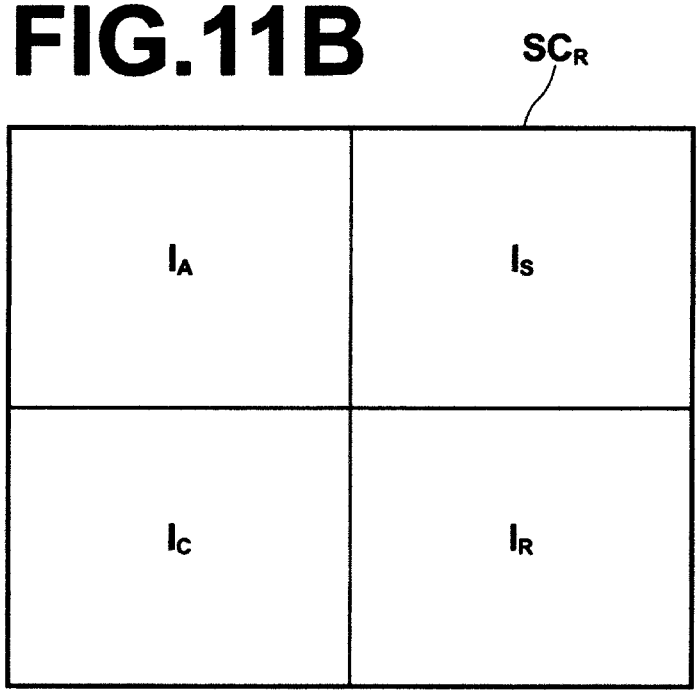
FIG. 11B illustrates, by way of example, a layout of right eye parallax image and three orthogonal cross-sectional images in a right eye display screen.
Figure 11C:
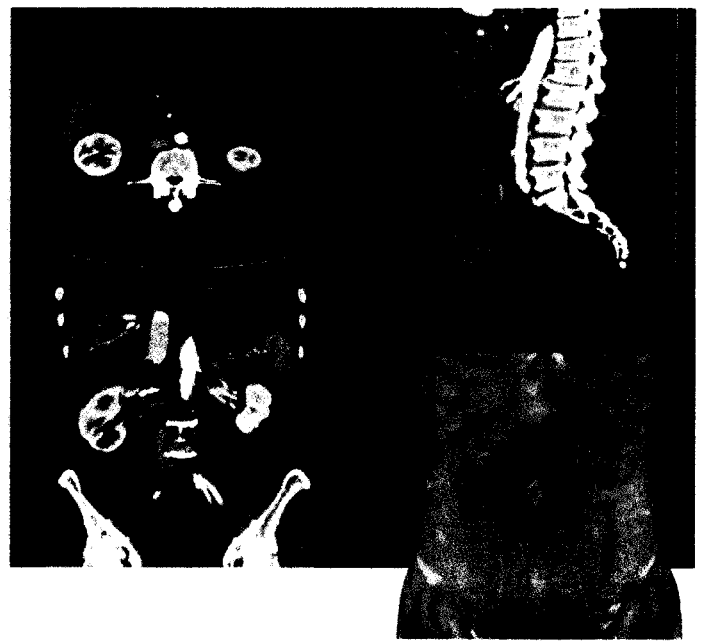
FIG. 11C schematically illustrates, by way of example, a mixed display of non-stereoscopic three orthogonal cross-sectional images and a stereoscopic volume rendering image.

FIGS. 11A, 11B illustrate example settings of left eye display screen $SC_L$ and right eye display screens $SC_R$ respectively for a mixed display of a stereoscopic display based on left and right eye parallax images $I_L$, $I_R$ and a non-stereoscopic display based on three orthogonal cross-sectional images $I_A$, $I_C$, $I_S$. FIG. 11C schematically illustrates a screen displayed on stereoscopic viewing support display unit 4a based on the display screens $SC_L$, $SC_R$. The displayed screen corresponds to that displayed based on an initial display condition in step #45 in the flowchart of FIG. 9 or that displayed when checkboxes 22a for three orthogonal cross-sectional images and volume rendering image, and checkbox 22b for stereoscopic viewing in user interface area 22 of display screen 20 are all checked, as in FIG. 10.

As shown in FIGS. 11A, 11B, axial cross-sectional image $I_A$, coronal cross-sectional image $I_C$, and sagittal cross-sectional image $I_S$ are laid out in sub-areas 21a, 21b, 21c of each of the left eye display screen $SC_L$ and right eye display screen $SC_R$. Therefore, in each of display pixels corresponding to each of sub-areas 21a, 21b, 21c of stereoscopic viewing support display unit 4a, displays based on the same pixel value are performed on the left eye pixel and right eye pixel within each display pixel. As a result, three orthogonal cross-sectional images $I_A/I_C$, $I_S$ are non-stereoscopically displayed on stereoscopic viewing support display unit 4a, as shown in FIG. 11C. In the mean time, left eye parallax image $I_L$ is laid out in sub-area 21d of the left eye display screen $SC_L$ and right eye parallax image $I_R$ is laid out in sub-area 21d of right eye display screen $SC_R$. Therefore, in each of display pixels corresponding to sub-area 21d of stereoscopic viewing support display unit 4a, a display based on the pixel value of left eye parallax image $I_L$ is performed on the left eye pixel while a display based on the pixel value of right eye parallax image $I_R$ is performed on the right eye pixel within each display pixel. As a result, a volume rendering image based on the left eye parallax image $I_L$ and right eye parallax image $I_R$ is stereoscopically displayed on stereoscopic viewing support display unit 4a, as shown in FIG. 11C.

Figure 12A:
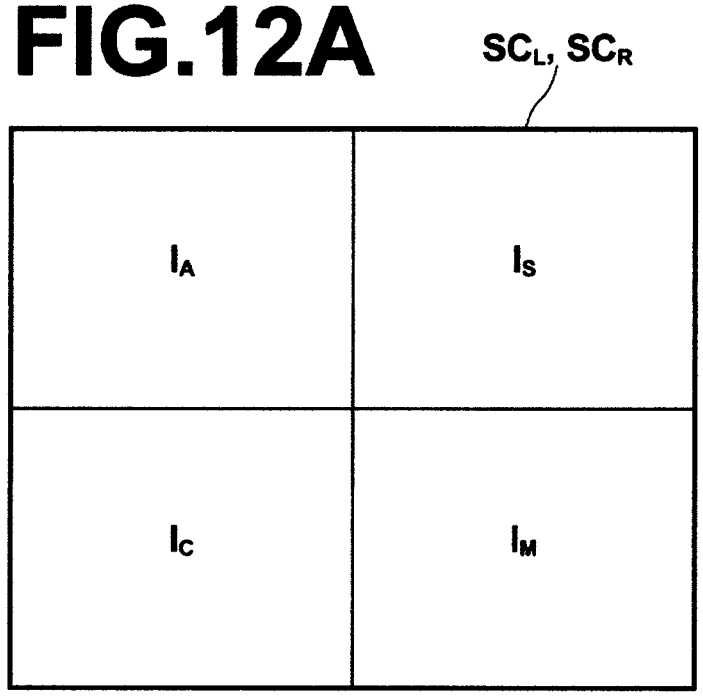
FIG. 12A schematically illustrates, by way of example, a layout of a non-stereoscopic image and three orthogonal cross-sectional images in a display screen for each eye.
Figure 12B:
FIG. 12B illustrates, by way of example, non-stereoscopic display of a volume rendering image and three orthogonal cross-sectional images.

FIG. 12A illustrates example settings of left eye display screen $SC_L$ and right eye display screens $SC_R$ for a non-stereoscopic display of a volume rendering image based on non-stereoscopic viewing image $I_M$ and a non-stereoscopic display based on three orthogonal cross-sectional images $I_A$, $I_C$, $I_S$ without performing a stereoscopic display. FIG. 12B schematically illustrates a screen displayed on stereoscopic viewing support display unit 4a based on the display screens $SC_L$, $SC_R$. The displayed screen corresponds to that displayed when checkboxes 22a for three orthogonal cross-sectional images and volume rendering image are checked while checkbox 22b for stereoscopic viewing is not checked in user interface area 22 of display screen 20 shown in FIG. 10.

As shown in FIG. 12A, axial cross-sectional image $I_A$, coronal cross-sectional image $I_C$, and sagittal cross-sectional image $I_S$ are laid out in sub-areas 21a, 21b, 21c and non-stereoscopic viewing image $I_M$ is laid out in sub-area 21d of each of the left eye display screen $SC_L$ and right eye display screen $SC_R$. Therefore, in each of display pixels corresponding to each of sub-areas 21a, 21b, 21c, 21d of stereoscopic viewing support display unit 4a, displays based on the same pixel value are performed on the left eye pixel and right eye pixel within each display pixel. As a result, three orthogonal cross-sectional images $I_A$, $I_C$, $I_S$ and non-stereoscopic viewing image $I_M$ are non-stereoscopically displayed on stereoscopic viewing support display unit 4a, as shown in FIG. 12B. As described in the first embodiment, the display of non-stereoscopic viewing image $I_M$ is a non-stereoscopic display equivalent to a stereoscopic display of a volume rendering image based on left eye parallax image $I_L$ and right eye parallax image $I_R$.

Figure 13A:
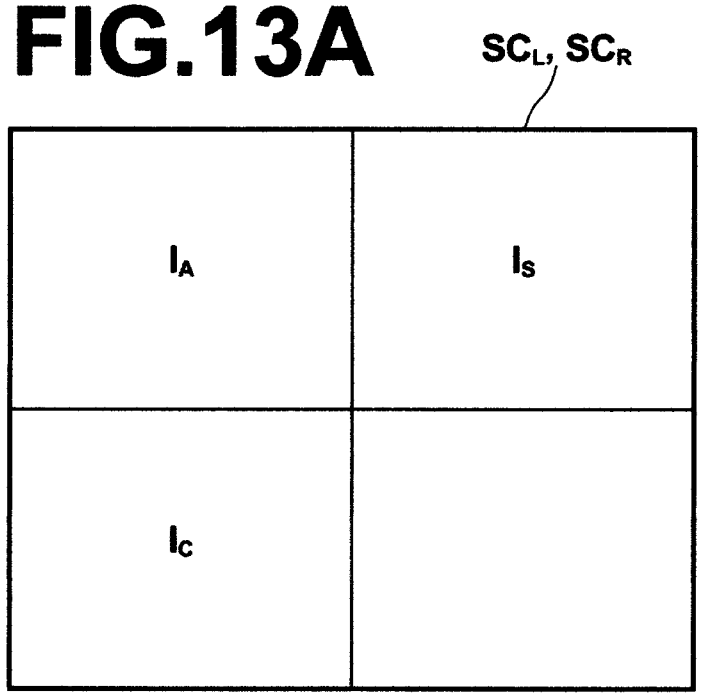
FIG. 13A illustrates, by way of example, a layout of three orthogonal cross-sectional images in a display screen for each eye.
Figure 13B:
FIG. 13B schematically illustrates, by way of example, a non-stereoscopic display of only three orthogonal cross-sectional images.

FIG. 13A illustrates example settings of left eye display screen $SC_L$ and right eye display screens $SC_R$ for only a non-stereoscopic display based on three orthogonal cross-sectional images $I_A$, $I_c$, $I_s$ without performing a stereoscopic display. FIG. 13B schematically illustrates a screen displayed on stereoscopic viewing support display unit 4a based on the display screens $SC_L$, $SC_R$. The displayed screen corresponds to that displayed when checkbox 22a for three orthogonal cross-sectional images (upper side) is checked while checkbox 22a for volume rendering image and checkbox 22b for stereoscopic viewing are not checked in user interface area 22 of display screen 20 shown in FIG. 10.

As shown in FIG. 13A, axial cross-sectional image $I_A$/coronal cross-sectional image $I_C$, and sagittal cross-sectional image $I_S$ are laid out in sub-areas 21a, 21b, 21c of each of the left eye display screen $SC_L$ and right eye display screen $SC_R$. Therefore, in each of display pixels corresponding to each of sub-areas 21a, 21b, 21c of stereoscopic viewing support display unit 4a, displays based on the same pixel value are performed on the left eye pixel and right eye pixel within each display pixel.

Figure 14A:
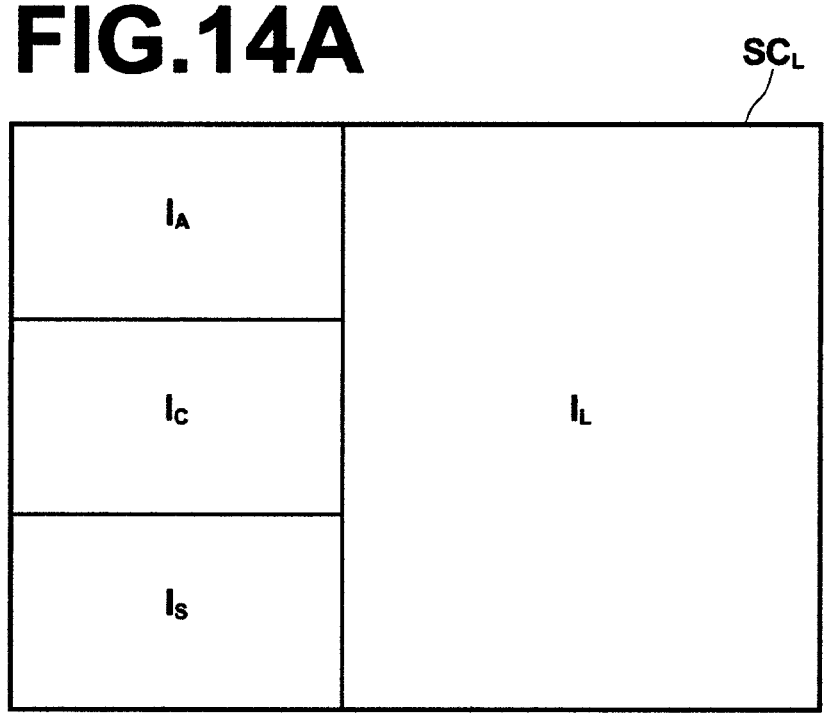
FIG. 14A illustrates, by way of example, a layout of left eye parallax image and three orthogonal cross-sectional images in a left eye display screen.
Figure 14B:
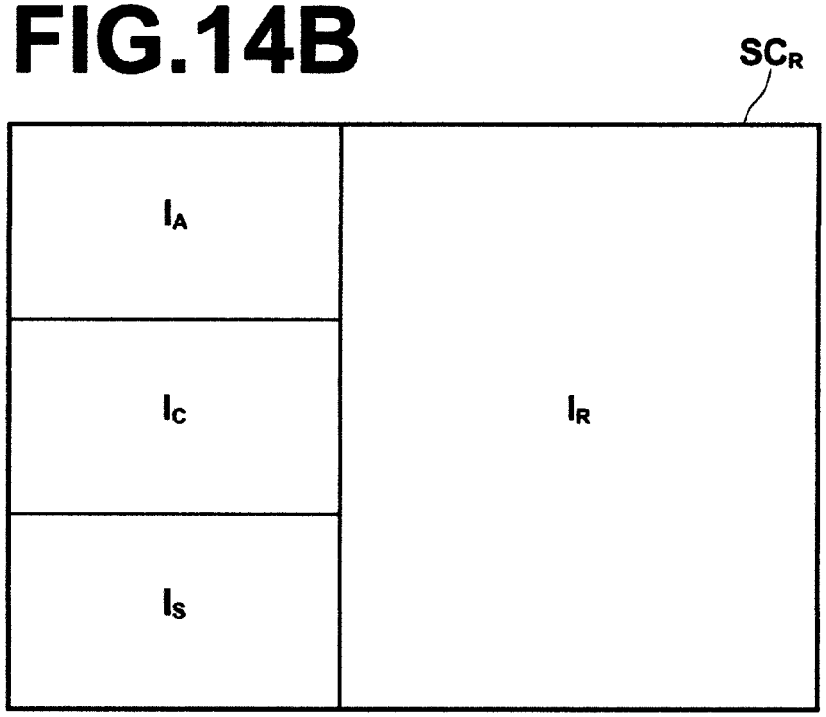
FIG. 14B illustrates, by way of example, a layout of right eye parallax image and three orthogonal cross-sectional images in a right eye display screen.
Figure 14C:
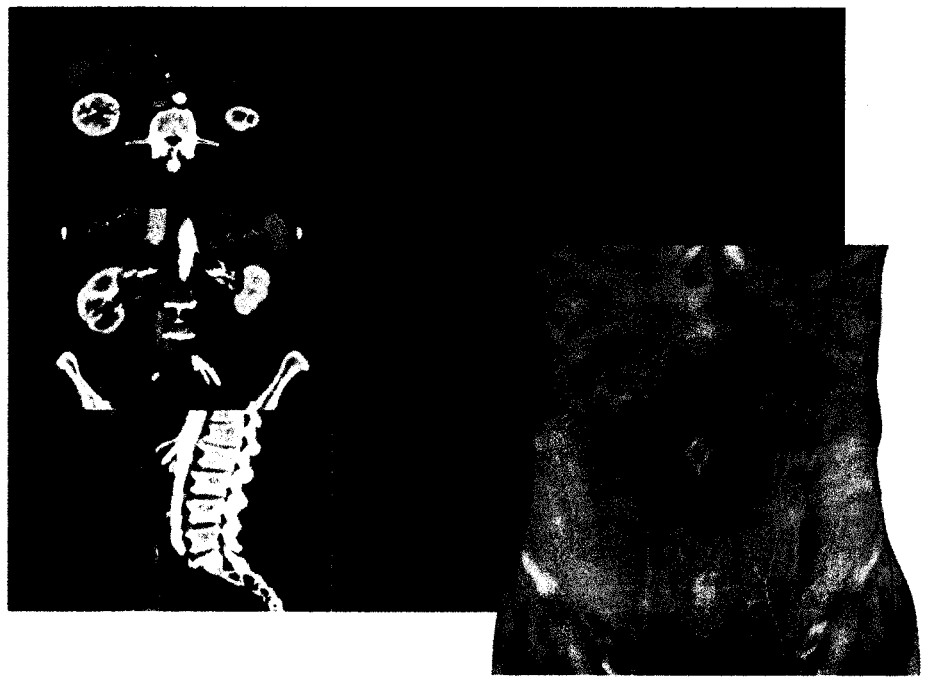
FIG. 14C schematically illustrates another example of a mixed display of non-stereoscopic three orthogonal cross-sectional images and a stereoscopic volume rendering image.

FIGS. 14A to 14C illustrate a case in which selection of radio buttons 22c for selecting a layout of image display area 21 is changed from the layout shown on the left to the layout shown in the center in the same setting state as that in user interface area 22 of display screen 20 shown in FIG. 10. As shown in FIGS. 14A, 14B, the layout in which the display area is equally divided into a 2×2 matrix form to the layout in which the display area is divided into four areas, including three equally divided areas of the left half and the remaining right half. In each of left eye display screen $SC_L$ and right eye display screen $SC_R$, three orthogonal cross-sectional images $I_A$, $I_C$/$I_s$ are laid out in the three sub-areas of the left half of image display area. Further, left eye parallax image $I_L$ is laid out in the right half area of left eye display screen $SC_L$ while right eye parallax image $I_R$ is laid out in the right half area of right eye display screen $SC_R$. This will result in that, in each of display pixels corresponding to the left half of the image display area 21 of stereoscopic viewing support display unit 4a, displays based on the same pixel value are performed on the left eye pixel and right eye pixel within each display pixel, whereby three orthogonal cross-sectional images $I_A$, $I_C$, $I_S$ are non-stereoscopically displayed on stereoscopic viewing support display unit 4a, as shown in FIG. 14C. In the mean time, left eye parallax image $I_L$ is laid out in the right half of left eye display screen $SC_L$ and right eye parallax image $I_R$ is laid out in the right half of right eye display screen $SC_R$, so that, in each of display pixels corresponding to the right half of image display area 21 of stereoscopic viewing support display unit 4a, a display based on the pixel value of left eye parallax image $I_L$ is performed on the left eye pixel while a display based on the pixel value of right eye parallax image $I_R$ is performed on the right eye pixel within each display pixel. As a result, a volume rendering image based on the left eye parallax image $I_L$ and right eye parallax image $I_R$ is stereoscopically displayed on stereoscopic viewing support display unit 4a, as shown in FIG. 14C.

Figure 15:
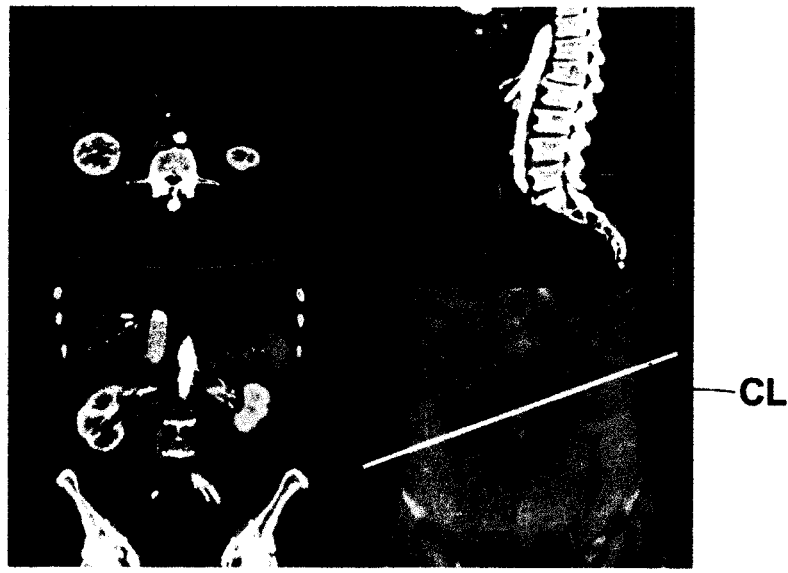
FIG. 15 illustrates, by way of example, an image display when a cross-section for performing cutting on a stereoscopically displayed image in the visual line direction.

FIG. 15 shows an example of display when image editing button 22e (left side) for performing cutting on a stereoscopically displayed image in the visual line direction is pressed. As shown in FIG. 15, when image editing button 22e (left side) for performing cutting on a stereoscopically displayed image in the visual line direction is pressed by the user using the pointing device or the like, the display is switched from the mixed display of stereoscopic display based on left and right eye parallax images $I_L$, $I_R$ and the non-stereoscopic display based on three orthogonal cross-sectional images $I_A$/$I_C$, $I_S$ shown in FIG. 11C to the non-stereoscopic display of non-stereoscopic viewing image $I_M$ and three orthogonal cross-sectional images $I_A$, $I_C$, $I_S$ shown in FIG. 12B. The user may set a cutting plane CL on the non-stereoscopically displayed non-stereoscopic viewing image $I_M$ in sub-area 21d using the pointing device or the like. Cross-sectional image generation unit 14 generates a cross-sectional image of a cross-section that passes through the determined cutting plane CL and is parallel to the visual line direction of the non-stereoscopic viewing image $I_M$ ($VL_M$ in FIG. 5), and display control unit 15, for example, generates a new image display window different from that shown in FIG. 10 and causes the generated cross-sectional image based on the cutting plane CL to be displayed in the window.

Figure 16:
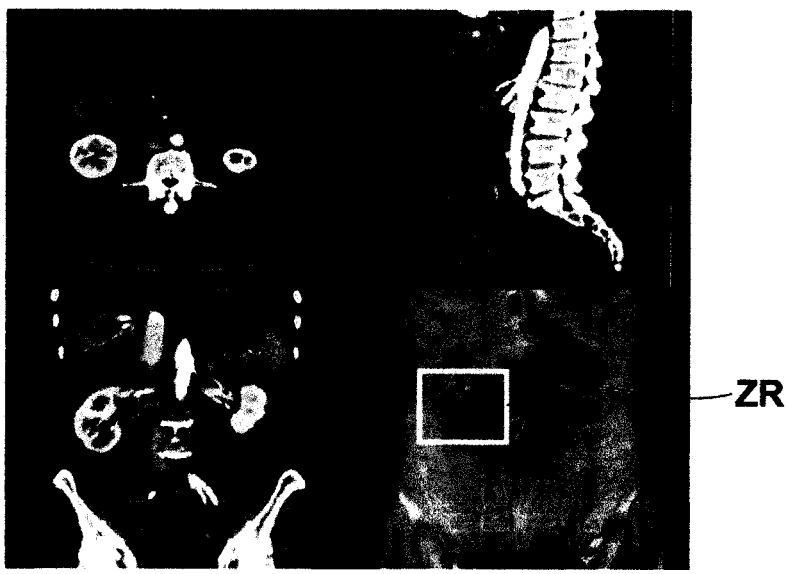
FIG. 16 illustrates, by way of example, an image displayed when setting a region of attention for performing a zoom display of a local area with respect to a stereoscopically displayed image.

FIG. 16 shows an example of display when image editing button 22e (right side) for performing a zoom display of an area of attention is pressed. As shown in FIG. 16, when image editing button 22e (right side) for performing a zoom display of an area of attention is pressed by the user using the pointing device or the like, the display is also switched from the mixed display of stereoscopic display based on left and right eye parallax images $I_L$, $I_R$ and the non-stereoscopic display based on three orthogonal cross-sectional images $I_A$, $I_C$, $I_S$ shown in FIG. 11C to the non-stereoscopic display of non-stereoscopic viewing image $I_M$ and three orthogonal cross-sectional images $I_A$, $I_C$, $I_S$ shown in FIG. 12B. The user may specify an area of attention ZR in the non-stereoscopically displayed non-stereoscopic viewing image $I_M$ in sub-area 21d using the pointing device or the like. Using the three-dimensional area of the three-dimensional medical image V corresponding to the specified area of attention ZR as input, stereoscopic viewing image generation unit 11 of the image processing workstation generates enlarged parallax images of the respective eyes with a higher resolution than that of the previously displayed left eye parallax image $I_L$ and right eye parallax image $I_R$ based on the left eye viewpoint position $VP_L$ and right eye viewpoint position $VP_R$. Then display control unit 15, for example, generates a new image display window different from that shown in FIG. 10 and causes the area corresponding to the area of attention ZR to be stereoscopically displayed in the window in an enlarged form based on the generated parallax images of the respective eyes.

As described above, display control unit 15 may cause stereoscopic viewing support display unit 4a to perform display by changing the type of image to be displayed, display method (stereoscopic or non-stereoscopic), and display layout in response to user operation of various types of interfaces provided in user interface area 22 shown in FIG. 10. Switching of the display mode may be implemented, for example, in the following manner. That is, when a pointer operated by the pointing device of stereoscopic viewing support display unit 4a is moved to an area in which an image is stereoscopically displayed (sub-area 21d in the example of FIGS. 11A to 11C), left and right eye parallax images $I_L$, $I_R$ in the stereoscopic display areas of the left eye display screen $SC_L$ and right eye display screen $SC_R$ are changed to the non-stereoscopic viewing image $I_M$, thereby switching the image display in the area from stereoscopic display to non-stereoscopic display. Conversely, when the pointer is moved outside of an area in which non-stereoscopic viewing image $I_M$ is displayed (sub-area 21d in FIGS. 12A, 12B), non-stereoscopic viewing images $I_M$ in the areas of the left eye display screen $SC_L$ and right eye display screen $SC_R$ are respectively changed to left and right eye parallax images $I_L$, $I_R$ corresponding to the non-stereoscopic viewing image $I_M$, thereby switching the image display in the area from non-stereoscopic display to stereoscopic display.

As described above, in the second embodiment of the present invention, display control unit 15 selectively outputs left and right eye parallax images $I_L$, $I_R$ generated by stereoscopic viewing image generation unit 11 and non-stereoscopic viewing image $I_M$ generated by non-stereoscopic viewing image generation unit 12 based on an initial display condition and another display condition set by a user operation. This allows a stereoscopic viewing image or a non-stereoscopic viewing image to be outputted flexibly and appropriately according to the intended use.

More specifically, if the non-stereoscopic viewing image $I_M$ is displayed when a cutting plane for cutting in the visual line direction or an area of attention for local enlargement display is to be set to a stereoscopically displayed image, the setting operation can be performed on the non-stereoscopic viewing image $I_M$ equivalent to the stereoscopic image. Consequently, when performing the operation described above, unpleasant feeling due to a material difference of visual line from the visual line for viewing the stereoscopic image, such as the case in which either one of the parallax images $I_L$, $I_R$ is outputted for performing the operation is eliminated or the case in which a position different from the position desired by the user is specified in the operation described above is prevented, whereby the operability is improved.

Note that, in the second embodiment, left and right eye parallax images $I_L$, $I_R$ for stereoscopic viewing and non-stereoscopic viewing image $I_M$ may be caused, by display control unit 15, to be generated as required, as in the first embodiment.

Further, in the second embodiment, the initial display condition in step #45 is not limited to that for performing the display shown in FIGS. 11A to 11C, and the initial display condition may be that for performing the display shown in FIGS. 12A, 12B, that for performing the display shown in FIGS. 13A, 13B, or that for performing the display shown in FIGS. 14A to 14C.

In the second embodiment described above, when performing the cutting in the visual line direction shown in FIG. 15 shown in FIG. 16 and the enlargement of an area of attention shown in FIG. 16, the display in sub-area 21d is switched from a stereoscopic display based on left and right eye parallax images $I_L$, $I_R$ to a non-stereoscopic display based on non-stereoscopic viewing image $I_M$. But display screen information using the non-stereoscopic viewing image $I_M$ shown in FIG. 12A may be stored in a predetermined memory area for position control of the pointing device, and while continuing the stereoscopic display based on left and right eye parallax images $I_L$, $I_R$ in the sub-area 21d, the position of the cutting plane CL or the position of the area of attention ZR may be internally identified using the display screen information for position control of the pointing device in the movement operation of the pointer by the pointing device and the setting operation of cutting plane CL and area of attention ZR.

More specifically, the position of the pointer of the pointing device is detected in the non-stereoscopic viewing image $I_M$ in the display screen information for position control, a position corresponding to the detected position is identified on a projection plane to which the non-stereoscopic viewing image $I_M$ is projected in the coordinate space of three-dimensional medical image V, then searching is performed on the visual line connecting between the corresponding point on the projection plane and the equivalent viewpoint position $VP_M$ from the equivalent viewpoint position $VP_M$ toward the three-dimensional medical image V, and a point where the integrated value of opacity based on the ray casting process exceeds a predetermined threshold value may be determined to be the position (three-dimensional position) of the pointer in the coordinate space of the three-dimensional medical image V. Here, when performing the searching, a point where the opacity or pixel value changes more rapidly than a predetermined threshold value or a point where the opacity or pixel value exceeds a predetermined threshold value may be detected and determined to be the three-dimensional position of the pointer. Further, where the non-stereoscopic viewing image $I_M$ is generated by a MIP method, a point where the pixel value becomes maximal may be determined to be the three-dimensional position of the pointer. If a point on a projection plane to which a pixel on a visual line passing through the three-dimensional position of the pointer and left eye viewpoint position $VP_L$ is projected is identified and a pointer (arrow mark or the like) is displayed at the position in the left eye parallax image $I_L$ corresponding to the identified position, then, likewise, a point on a projection plane to which a pixel on a visual line passing through the three-dimensional position of the pointer and right eye viewpoint position $VP_R$ is projected is identified and a pointer is displayed at the position in the right eye parallax image $I_R$ corresponding to the identified position, the pointer can be stereoscopically displayed in the sub-area 21d. In the method of determining the three-dimensional position of the pointer, the opacity or pixel value may not satisfy the threshold conditions described above in an area of the three-dimensional medical image V in which the subject is not present. In such a case, the pointer may not be displayed or the pointer may be non-stereoscopically displayed based on the position of the pointer in the non-stereoscopic viewing image $I_M$ for position control. In such a case, the display mode, such as the color or shape, of the pointer may be changed between the stereoscopic display and non-stereoscopic display.

In this way, while continuing the stereoscopic display in the sub-area 21d based on the left and right eye parallax images $I_L$, $I_R$, if the position of the pointer, cutting plane CL, or area of attention ZR is internally identified using the non-stereoscopic viewing image $I_M$ in the display screen information for position control of the pointing device in the moving operation of the pointer by the pointing device and setting operation of the cutting plane CL or of the area of attention ZR, and further the position of the pointer or the like is also stereoscopically displayed, the positional relationship of structures in the depth direction inside of the subject can be accurately recognized by the stereoscopic display and various operations by the pointing device can be performed in the depth direction. This may prevent an unintended user operation, such as an erroneous specification of an unintended structure in front instead of an intended blood vessel located at the back, resulting in improved operability.

The pointer of the pointing device may always be non-stereoscopically displayed based on the position of the pointer in the non-stereoscopic viewing image $I_M$ for position control. In this case, the display mode of the pointer may be changed between an area where the subject is present and the other area of the non-stereoscopic viewing image $I_M$.

Figure 17:
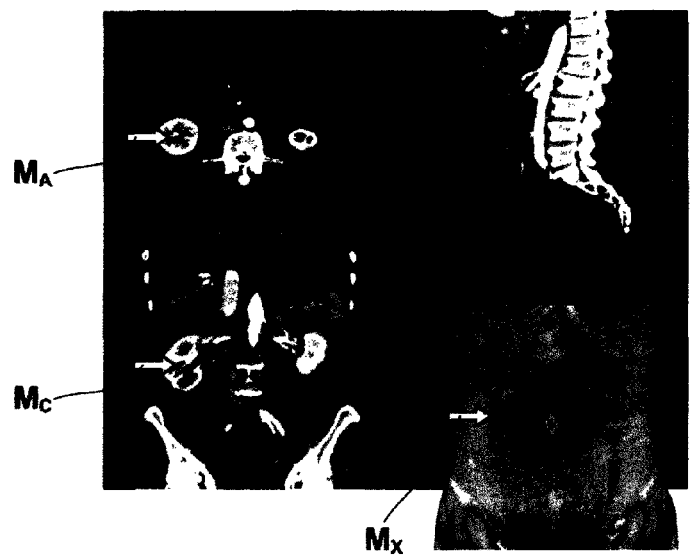
FIG. 17 illustrates, by way of example, an interlocking display of an annotation in a non-stereoscopically displayed cross-sectional image and an annotation in a stereoscopically displayed volume rendering image.

For example, when a user operation for adding an annotation to any one of the non-stereoscopically displayed images is performed on the screen display, including a stereoscopic display, like that as shown in FIG. 11C using an annotation button 22d shown in FIG. 10, display control unit 15 may be a unit that identifies the position of the added annotation in the three-dimensional medical image V, and adds and displays an identical annotation to the corresponding position in other cross-sectional images and the stereoscopically displayed image. FIG. 17 shows an example display in which, in response to an operation of adding an arrow shaped annotation $M_A$ to the axial cross-sectional image $I_A$, arrow shaped annotations $M_C$, $M_X$ are added to the corresponding positions in the coronal cross-sectional image $I_C$ and the stereoscopically displayed image respectively. Here, the annotation $M_X$ is added to the corresponding positions in the original left and right eye parallax images $I_L$, $I_R$ for stereoscopic display, whereby it is stereoscopically displayed.

The embodiments described above are illustration purposes only and many not be construed as limiting the scope of the technical scope of the present invention.

It should be appreciated that various modifications and changes made to the system configurations, hardware configurations, processing flows, module structures, user interfaces, specific processing contents, and the like in the embodiments described above without departing from the spirit of the present invention are included in the scope of the present invention.

For example, with respect to the system configurations, a description has been made of a case in which various types of processing shown in FIGS. 2 and 8 are performed by single image processing workstation 4, but the system may be configured such that the various types of processing is distributed to a plurality of workstations and performed in cooperation with each other. With respect to the hardware configurations, the stereoscopic display method is not limited to that described above, and a method using glasses having a special optical property such as the stereo viewer described in Japanese Unexamined Patent Publication No. 62 (1987)-016741 or a method using a three-dimensional display pixel array. Further, one parallax image is used for each of left and right eyes for stereoscopic display, but multiple of parallax images may be displayed on each of left and right sides as described in "Research & Development of Stereoscopic Display", Takaki Lab., Tokyo University of Agriculture and Technology, Faculty of Technology, Department of Electrical Engineering, URL: http://www.tuat.ac.jp/e-takaki/display/display.html.

Further, the switching between stereoscopic display and non-stereoscopic display may be performed in software through an operation at the user interface as in the second embodiment described above or in hardware through a switch or the like on the display unit side.

With respect to the processing flows, image generation processing in steps #2 and #3 in the flowchart of FIG. 3, and image generation processing in steps #42 to #44 may be performed in parallel as in each flowchart or in series and the processing order may be changed.

With respect to the module structure, the first and second embodiments may be combined to implement both of the switching between a stereoscopic display and a non-stereoscopic display at stereoscopic viewing support display unit 4a (second embodiment) and switching between a stereoscopic display and a non-stereoscopic display for each output destination device (first embodiment).

With respect to specific processing contents, stereoscopic viewing image generation unit 11 and non-stereoscopic viewing image generation unit 12 may generate an image by a method other than volume rendering methods, such as MIP method, MinIP method, MPR method, and the like. That is, the image to be generated may be a pseudo three-dimensional image having information of a depth direction or a two-dimensional image. An area for stereoscopic viewing and an area for non-stereoscopic viewing may be provided in the left and right eye parallax images $I_L$, $I_R$ for stereoscopic viewing. For example, if left and right eye parallax images $I_L$, $I_R$ are generated by extracting a stereoscopic viewing target coronary artery by a known method based on a three-dimensional medical image V representing the heart of a subject, generating parallax images of left and right viewpoints $VP_L$, $VP_R$ only for the extracted coronary artery, generating images viewed from the equivalent viewpoint position $VP_M$ as the left and right parallax images for the hear portion other than the coronary artery, and superimposing parallax images and the images representing the hear portion on top of each other respectively, a stereoscopic display of the coronary artery and a non-stereoscopic display of the heart portion other than the coronary artery can be realized in an image representing the entirety of the heart.

Further, if three-dimensional medical images V obtained at different time phases are used as input, then, based on the input, left and right eye parallax images $I_L$, $I_R$ and non-stereoscopic viewing image $I_M$ are generated for each time phase, and each generated image is switched and displayed in time-series manner, a motion picture like display can be realized. In particular, when the switching display is performed by synchronizing the left and right parallax images $I_L$, $I_R$, a stereoscopic motion picture like display can be realized.

Figure 18:
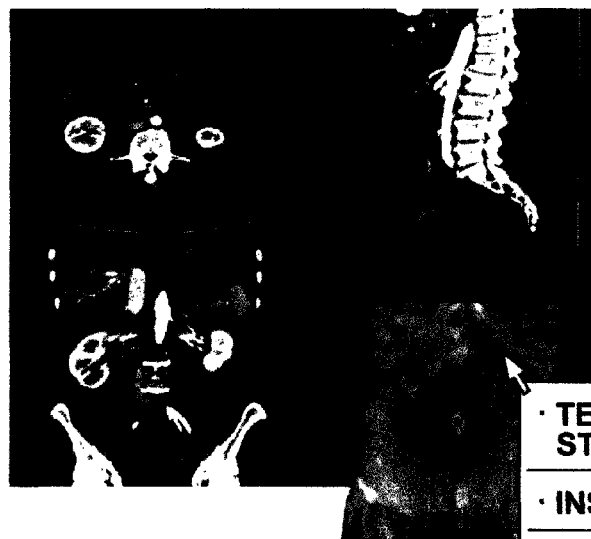
FIG. 18 illustrates a pointer of a pointing device and an example of sub-menu.
Figure 19:
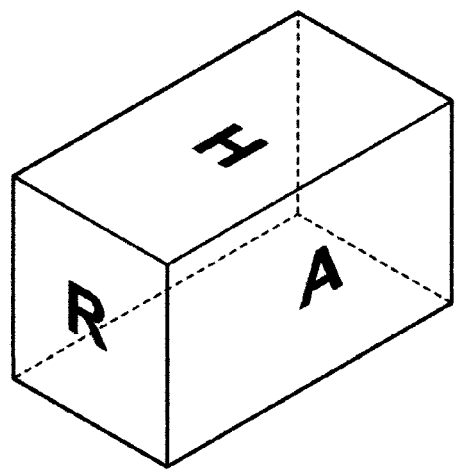
FIG. 19 illustrates, by way of example, an icon representing orientations of a subject.

Still further, when performing a stereoscopic display, display control unit 15 may be configured to stereoscopically display not only an image representing a subject but also, for example, a sub-menu displayed when the pointing device of image processing workstation 4 is right-clicked on the stereoscopically displayed image, as shown in FIG. 18, or an icon indicating the orientation of the subject (H for head side, A for anterior side, and R for right side), as shown in FIG. 19.

What is claimed is:

1. A stereoscopic viewing medical image generation apparatus, comprising:
   a stereoscopic viewing image generation unit configured for, using a three-dimensional medical image representing a subject as input, generating a stereoscopic viewing image for stereoscopic output of the subject based on a given image generation condition, a given image generation condition of the image generation unit including a number of parallax images of the stereoscopic viewing image, viewpoint positions of the stereoscopic viewing image, visual line directions of the stereoscopic viewing image, projecting with parallel projection or central projection, and image generation;
   a non-stereoscopic viewing image generation unit configured for generating a non-stereoscopic viewing image for non-stereoscopic output equivalent to the stereoscopic output based on the three-dimensional medical image and the image generation condition of the stereoscopic viewing image;
   a selective output unit configured for selectively outputting the stereoscopic viewing image and the non-stereoscopic viewing image based on a predetermined output image selection condition; and
   a cross-sectional image generation unit configured for generating a cross-sectional image based on three-dimensional medical image and position information, wherein
   an output destination device of the selective output unit is capable of selectively presenting a stereoscopic display based on the stereoscopic viewing image and a non-stereoscopic display based on the non-stereoscopic viewing image,
   the output image selection condition is a condition that, when an operation of an input device involving specification of a desired position in the stereoscopic viewing image stereoscopically displayed on the display device is detected, causes the non-stereoscopic viewing image to be outputted,
   the operation is an operation for specifying position that is a part of the three-dimensional medical image to stereoscopically display or an operation for specifying position to generate cross-sectional image, and
   after receiving the desired position specified on the non-stereoscopic viewing image after the operation, the selective output unit generates a stereoscopic viewing image corresponding to the specified position by the stereoscopic viewing image generation unit or generates a non-stereoscopic viewing image corresponding to the specified position by the non-stereoscopic viewing image generation unit based on the operation.

2. The stereoscopic viewing image generation apparatus of claim 1, wherein the display device is further capable of displaying a screen in which stereoscopic display and non-stereoscopic display are presented in a mixed manner.

3. The stereoscopic viewing image generation apparatus of claim 2, wherein:
   the selective output unit causes the display device to display a screen in which the cross-sectional image and the stereoscopic viewing image or the non-stereoscopic viewing image are presented in a mixed manner.

4. The stereoscopic viewing image generation apparatus of claim 1, wherein the stereoscopic viewing image is constituted by a plurality of parallax images representing the subject viewed from different viewpoints.

5. The stereoscopic viewing image generation apparatus of claim 4, wherein each parallax image is a projection image obtained by projecting at least one pixel value of a plurality of points on a visual line extending from the viewpoint of the parallax image toward the subject.

6. The stereoscopic viewing image generation apparatus of claim 5, wherein the parallax image is a pseudo three-dimensional image representing depth direction information of the subject.

7. The stereoscopic viewing image generation apparatus of claim 4, wherein the non-stereoscopic viewing image is an image representing the subject viewed from a single viewpoint equivalent to a plurality of viewpoints of the plurality of parallax images.

8. The stereoscopic viewing image generation apparatus of claim 7, wherein the non-stereoscopic viewing image is a projection image obtained by projecting at least one pixel value of a plurality of points on a visual line extending from the single viewpoint toward the subject.

9. The stereoscopic viewing image generation apparatus of claim 8, wherein the non-stereoscopic viewing image is a pseudo three-dimensional image, representing depth direction information of the subject.

10. The stereoscopic viewing image generation apparatus of claim 1, wherein the stereoscopic viewing image is an image that includes a stereoscopic viewing area for stereoscopic display and a non-stereoscopic viewing area for non-stereoscopic display.

11. A stereoscopic viewing medical image generation apparatus, comprising:
    a stereoscopic viewing image generation unit configured for, using a three-dimensional medical image representing a subject as input, generating a stereoscopic viewing image for stereoscopic output of the subject based on a given image generation condition, a given image generation condition of the image generation unit including a number of parallax images of the stereoscopic viewing image, viewpoint positions of the stereoscopic viewing image, visual line directions of the stereoscopic viewing image, projecting with parallel projection or central projection, and image generation;
    a non-stereoscopic viewing image generation unit configured for generating a non-stereoscopic viewing image for non-stereoscopic output equivalent to the stereoscopic output based on the three-dimensional medical image and the image generation condition of the stereoscopic viewing image;
    a display controller adapted to cause the stereoscopic viewing image to be displayed on a display device capable of performing stereoscopic display, the display controller being configured to display a stereoscopic viewing image that is generated corresponding to the specified position by the stereoscopic viewing image generation unit; and
    an identifying unit, when an operation of an input device involving specification of a desired position in the stereoscopic viewing image stereoscopically displayed on the display device is performed, the specified position using the non-stereoscopic viewing image.

12. A stereoscopic viewing image generation method, comprising the steps of:
- a CPU generating, using a three-dimensional medical image representing a subject as input, a stereoscopic viewing image for stereoscopic output of the subject based on a given image generation condition, a given image generation condition including a number of parallax images of the stereoscopic viewing image, viewpoint positions of the stereoscopic viewing image, visual line directions of the stereoscopic viewing image, projecting with parallel projection or central projection, and image generation;
- the CPU generating a non-stereoscopic viewing image for non-stereoscopic output equivalent to the stereoscopic output based on the three-dimensional medical image and the image generation condition of the stereoscopic viewing image;
- selectively outputting with a selective output unit the stereoscopic viewing image and the non-stereoscopic viewing image based on a predetermined output image selection condition; and
- generating with a cross-sectional image generation unit a cross-sectional image based on three-dimensional medical image and position information, wherein
- an output destination device of the selective output unit is capable of selectively presenting a stereoscopic display based on the stereoscopic viewing image and a non-stereoscopic display based on the non-stereoscopic viewing image,
- the output image selection condition is a condition that, when an operation of an input device involving specification of a desired position in the stereoscopic viewing image stereoscopically displayed on the display device is detected, causes the non-stereoscopic viewing image to be outputted,
- the operation is an operation for specifying position that is a part of the three-dimensional medical image to stereoscopically display or an operation for specifying position to generate cross-sectional image, and
- after receiving the desired position specified on the non-stereoscopic viewing image after the operation, the selective output unit generates a stereoscopic viewing image corresponding to the specified position by a stereoscopic viewing image generation unit or generates a non-stereoscopic viewing image corresponding to the specified position of the non-stereoscopic viewing image generation unit based on the operation.

13. A non-transitory computer readable recording medium on which is recorded a stereoscopic viewing image generation program for causing a computer to perform the steps of:
- generating, using a three-dimensional medical image representing a subject as input, a stereoscopic viewing image for stereoscopic output of the subject based on a given image generation condition, a given image generation condition including a number of parallax images of the stereoscopic viewing image, viewpoint positions of the stereoscopic viewing image, visual line directions of the stereoscopic viewing image, projecting with parallel projection or central projection, and image generation;
- generating a non-stereoscopic viewing image for non-stereoscopic output equivalent to the stereoscopic output based on the three-dimensional medical image and the image generation condition of the stereoscopic viewing image;
- selectively outputting the stereoscopic viewing image and the non-stereoscopic viewing image based on a predetermined output image selection condition; and
- generating a cross-sectional image based on three-dimensional medical image and position information, wherein
- the program is capable of selectively presenting a stereoscopic display based on the stereoscopic viewing image and a non-stereoscopic display based on the non-stereoscopic viewing image,
- the output image selection condition is a condition that, when an operation of an input device involving specification of a desired position in the stereoscopic viewing image stereoscopically displayed on the display device is detected, causes the non-stereoscopic viewing image to be outputted,
- the operation is an operation for specifying position that is a part of the three-dimensional medical image to stereoscopically display or an operation for specifying position to generate cross-sectional image, and
- after receiving the desired position specified on the non-stereoscopic viewing image after the operation, a stereoscopic viewing image is generated corresponding to the specified position or generates a non-stereoscopic viewing image corresponding to the specified position based on the operation.

14. A stereoscopic viewing image generation method, comprising the steps of:
- with a stereoscopic viewing image generation unit, utilizing a three-dimensional medical image representing a subject as input, generating a stereoscopic viewing image for stereoscopic output of the subject based on a given image generation condition, a given image generation condition of the image generation unit including a number of parallax images of the stereoscopic viewing image, viewpoint positions of the stereoscopic viewing image, visual line directions of the stereoscopic viewing image, projecting with parallel projection or central projection, and image generation;
- with a non-stereoscopic viewing image generation unit, generating a non-stereoscopic viewing image for non-stereoscopic output equivalent to the stereoscopic output based on the three-dimensional medical image and the image generation condition of the stereoscopic viewing image;
- with a display controller, displaying the stereoscopic viewing image on a display device capable of performing stereoscopic display, the display controller being configured to display a stereoscopic viewing image that is generated corresponding to the specified position by the stereoscopic viewing image generation unit; and
- with an identifying unit, identifying when an operation of an input device involving specification of a desired position in the stereoscopic viewing image stereoscopically displayed on the display device is performed, the specified position using the non-stereoscopic viewing image.

15. A non-transitory computer readable recording medium on which is recorded a stereoscopic viewing image generation program for causing a computer to perform the steps of:
- utilizing a three-dimensional medical image representing a subject as input, generating a stereoscopic viewing image for stereoscopic output of the subject based on a given image generation condition, a given image generation condition including a number of parallax images of the stereoscopic viewing image, viewpoint positions of the stereoscopic viewing image, visual line directions of the stereoscopic viewing image, projecting with parallel projection or central projection, and image generation;

generating a non-stereoscopic viewing image for non-stereoscopic output equivalent to the stereoscopic output based on the three-dimensional medical image and the image generation condition of the stereoscopic viewing image;

displaying the stereoscopic viewing image on a display device capable of performing stereoscopic display, to display a stereoscopic viewing image that is generated corresponding to a specified position; and identifying when an operation of an input device involving specification of a desired position in the stereoscopic viewing image stereoscopically displayed on the display device is performed, the specified position using the non-stereoscopic viewing image.

* * * * *